United States Patent
Kikuchi et al.

(10) Patent No.: US 11,635,382 B2
(45) Date of Patent: Apr. 25, 2023

(54) BLOOD ANALYZER, BLOOD ANALYZING METHOD, AND PROGRAM

(71) Applicant: SYSMEX CORPORATION, Kobe (JP)

(72) Inventors: Osamu Kikuchi, Kobe (JP); Takahito Mihara, Kobe (JP); Yuji Masuda, Kobe (JP); Atsushi Shirakami, Kobe (JP); Takuma Watanabe, Kobe (JP); Daigo Fukuma, Kobe (JP); Masaharu Shibata, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 308 days.

(21) Appl. No.: 16/055,201

(22) Filed: Aug. 6, 2018

(65) Prior Publication Data
US 2019/0049383 A1 Feb. 14, 2019

(30) Foreign Application Priority Data

Aug. 10, 2017 (JP) .............................. JP2017-155938

(51) Int. Cl.
*G01N 21/64* (2006.01)
*G01N 15/14* (2006.01)
(Continued)

(52) U.S. Cl.
CPC ..... *G01N 21/6486* (2013.01); *G01N 15/1031* (2013.01); *G01N 15/1459* (2013.01);
(Continued)

(58) Field of Classification Search
CPC ...... G01N 1/28; G01N 15/14; G01N 15/1031; G01N 15/1434; G01N 15/1459;
(Continued)

(56) References Cited

U.S. PATENT DOCUMENTS

2003/0030783 A1* 2/2003 Roche .................. H04L 25/063
356/39
2008/0011684 A1* 1/2008 Dorian ................ A61M 1/3633
210/669
(Continued)

FOREIGN PATENT DOCUMENTS

CN 101236194 A 8/2008
CN 101846671 A 9/2010
(Continued)

OTHER PUBLICATIONS

Communication pursuant to Article 94(3) EPC dated Feb. 6, 2020 in a counterpart European patent application.
(Continued)

*Primary Examiner* — Matthew D Krcha
*Assistant Examiner* — Austin Q Le
(74) *Attorney, Agent, or Firm* — Metrolex IP Law Group, PLLC

(57) ABSTRACT

A blood analyzer according to one or more embodiments may include: a specimen preparation part that prepares a measurement specimen by mixing a reagent into a blood preparation; a measurement part that measures the measurement specimen; a measurement mode selection unit that receives an input of a type of blood preparation as a measurement target selected from a plurality of types of blood preparations; and a controller. The controller may cause the specimen preparation part to prepare the measurement specimen depending on the selected type of blood preparation.

18 Claims, 23 Drawing Sheets

(51) Int. Cl.
*G01N 33/80* (2006.01)
*G01N 33/96* (2006.01)
*G01N 35/00* (2006.01)
*G01N 15/10* (2006.01)
G01N 35/04 (2006.01)
G01N 33/49 (2006.01)
G01N 15/00 (2006.01)

(52) U.S. Cl.
CPC ......... *G01N 21/6428* (2013.01); *G01N 33/80* (2013.01); *G01N 33/96* (2013.01); *G01N 35/0099* (2013.01); *G01N 35/00722* (2013.01); G01N 33/49 (2013.01); G01N 2015/008 (2013.01); G01N 2015/0076 (2013.01); G01N 2015/0084 (2013.01); G01N 2015/1006 (2013.01); G01N 2021/6439 (2013.01); G01N 2035/00524 (2013.01); G01N 2035/00534 (2013.01); G01N 2035/00752 (2013.01); G01N 2035/00801 (2013.01); G01N 2035/00891 (2013.01); G01N 2035/0412 (2013.01)

(58) Field of Classification Search
CPC ........... G01N 15/6428; G01N 15/6486; G01N 33/48; G01N 33/49; G01N 33/80; G01N 33/96; G01N 35/00722; G01N 35/0099; G01N 2015/0076; G01N 2015/008; G01N 2015/0084; G01N 2015/1006; G01N 2035/00524; G01N 2035/00534; G01N 2035/00752; G01N 2035/00801; G01N 2035/00891; G01N 2035/0412; A61B 5/150755
See application file for complete search history.

(56) References Cited

U.S. PATENT DOCUMENTS

| | | | |
|---|---|---|---|
| 2010/0248300 A1 | 9/2010 | Yoshida et al. | |
| 2011/0104007 A1* | 5/2011 | Hirano | G01N 35/025 |
| | | | 422/63 |
| 2013/0171681 A1* | 7/2013 | Shibata | G01N 1/10 |
| | | | 435/29 |
| 2014/0356903 A1* | 12/2014 | Nagai | G01N 33/5094 |
| | | | 435/39 |
| 2015/0125900 A1 | 5/2015 | Nagai et al. | |

FOREIGN PATENT DOCUMENTS

| | | |
|---|---|---|
| CN | 103185776 A | 7/2013 |
| CN | 104805004 A | 7/2015 |
| EP | 2610621 A2 | 7/2013 |
| EP | 2735859 A2 | 5/2014 |
| EP | 2902769 A2 | 8/2015 |
| EP | 3001174 A1 | 3/2016 |
| JP | 2003-525456 A | 8/2003 |
| JP | 2006-292738 A | 10/2006 |
| JP | 2008-209383 A | 9/2008 |
| JP | 2008-209386 A | 9/2008 |
| JP | 2008-249424 A | 10/2008 |
| JP | 2011-521228 A | 7/2011 |
| JP | 4948230 B2 | 6/2012 |
| JP | 4994920 B2 | 8/2012 |
| JP | 2013-079888 A | 5/2013 |
| JP | 2013-140020 A | 7/2013 |
| JP | 2013-209333 A | 10/2013 |
| JP | 5457560 B2 | 4/2014 |
| JP | 2014-178334 A | 9/2014 |
| JP | 2017-035472 A | 2/2017 |
| WO | 9924831 A1 | 5/1999 |
| WO | 2017065280 A1 | 4/2017 |

OTHER PUBLICATIONS

Office Action dated Oct. 10, 2020 in a counterpart Chinese patent application.
Communication pursuant to Article 94(3) EPC dated Sep. 23, 2020 in a counterpart European patent application.
Office Action dated Jun. 1, 2021 for a counterpart Japanese patent application, with English translation.
Communication pursuant to Article 94(3) EPC dated May 26, 2021 for a counterpart European patent application.
Office Action("JPOA") dated Dec. 22, 2022 for a counterpart Japanese patent application.
Office Action dated Jan. 12, 2023 for a counterpart European patent application.

* cited by examiner

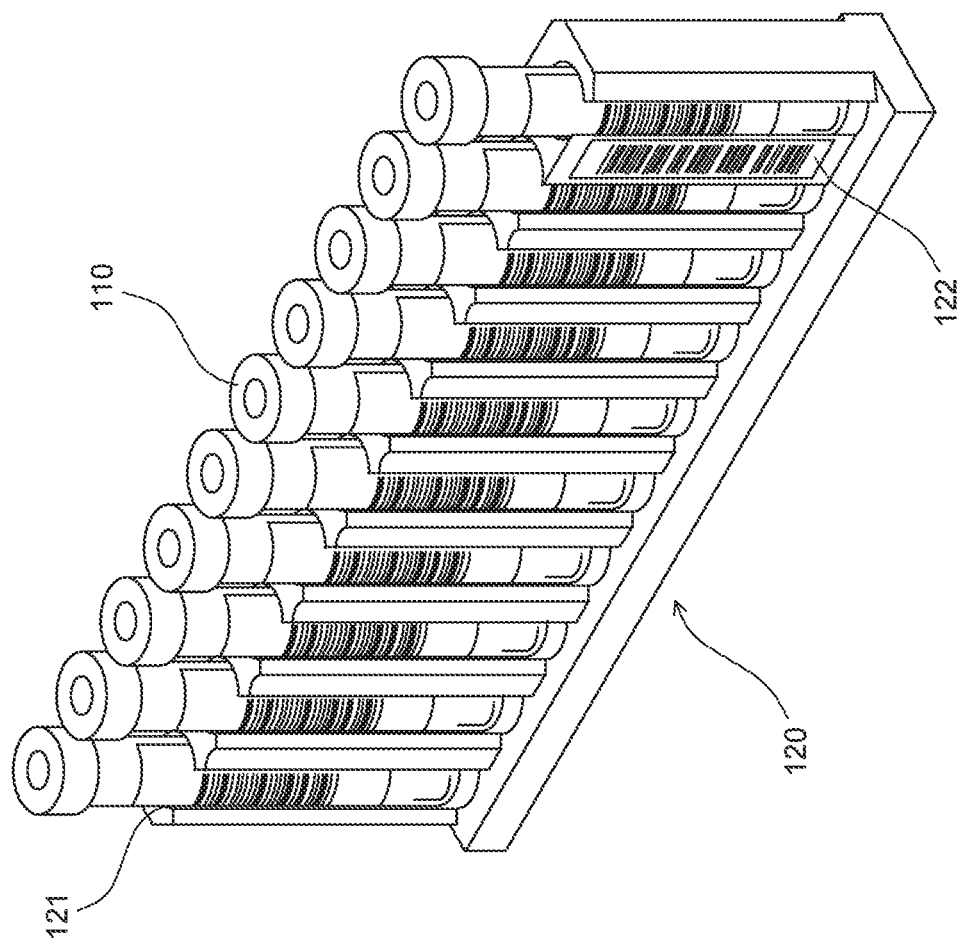
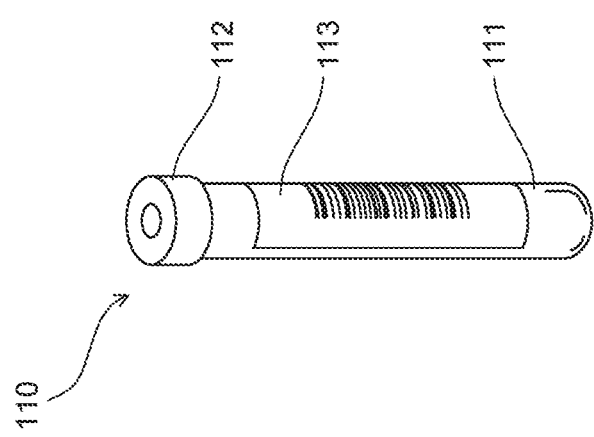
FIG. 2A
FIG. 2B

| LIQUID IN CONTAINER | NUMBER OF TIMES OF TURN OVER |
|---|---|
| WHOLE BLOOD | 8 |
| RED BLOOD CELL PREPARATION | 8 |
| PLASMA PREPARATION | 5 |
| PLATELET PREPARATION | 5 |

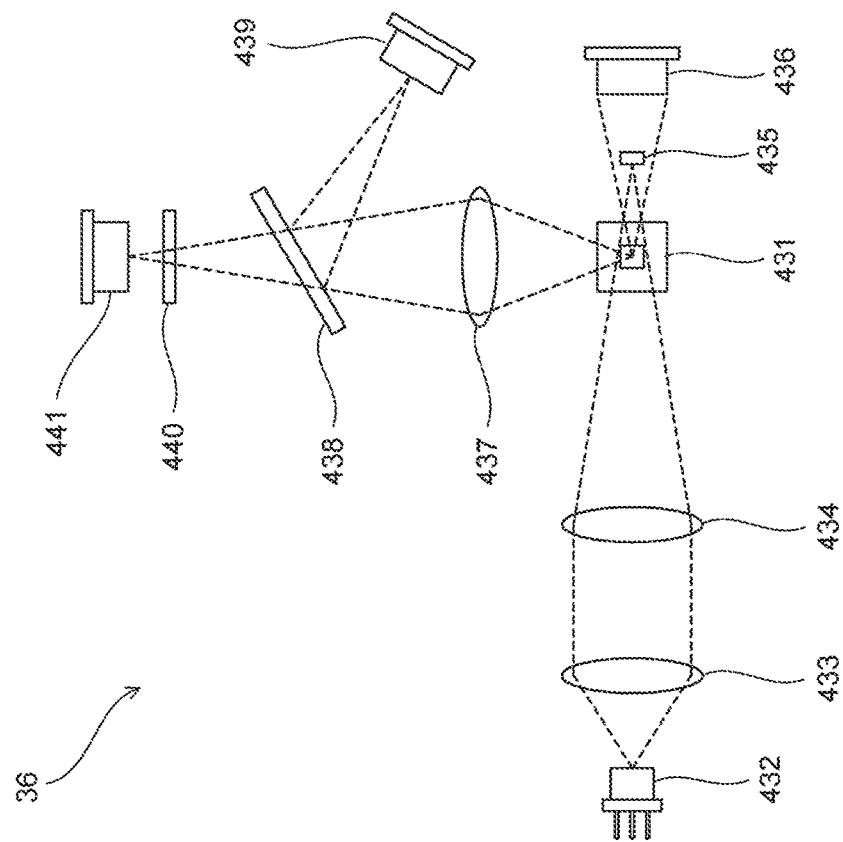
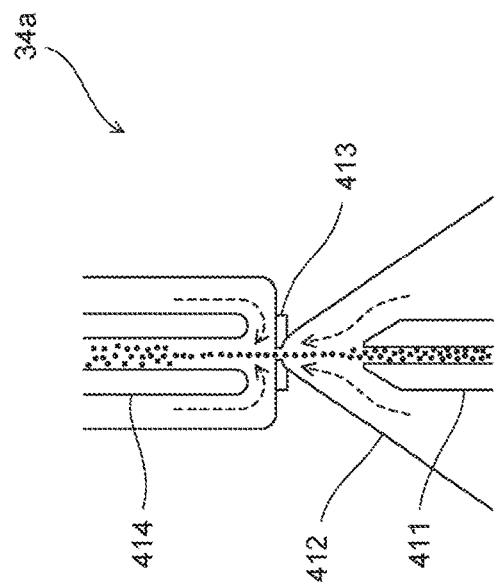
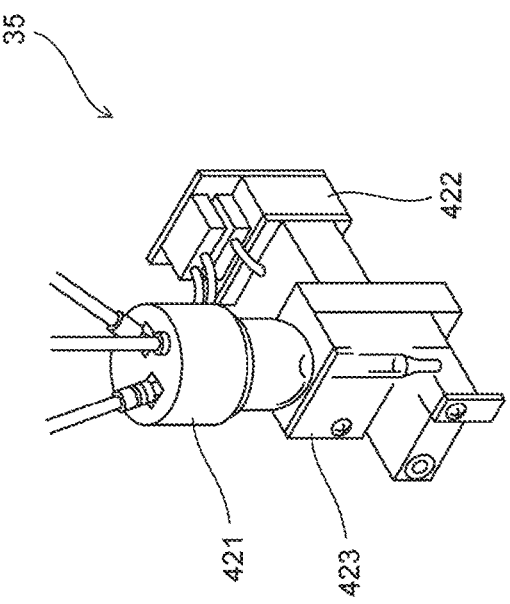
FIG. 6A
FIG. 6B
FIG. 6C

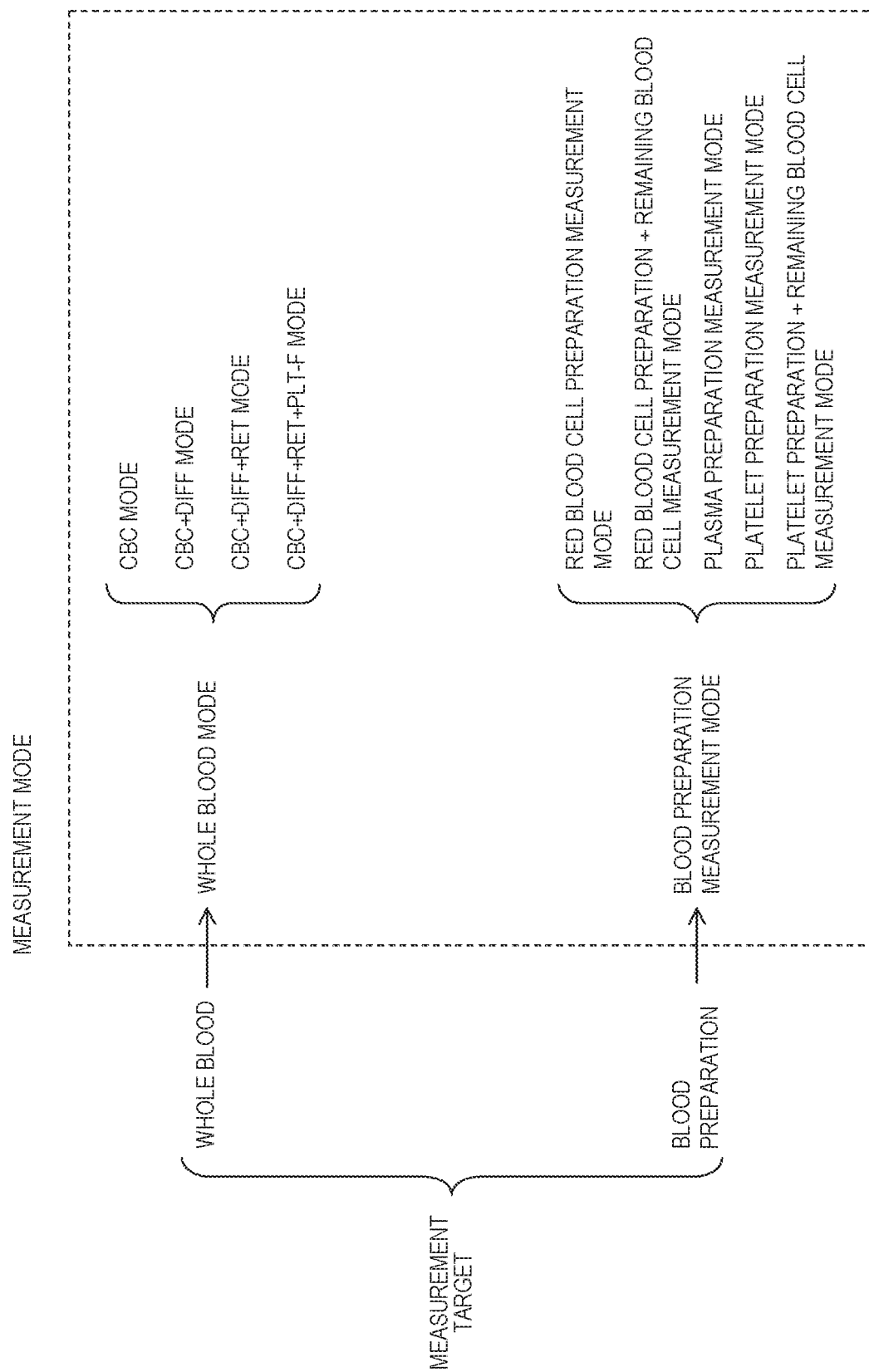

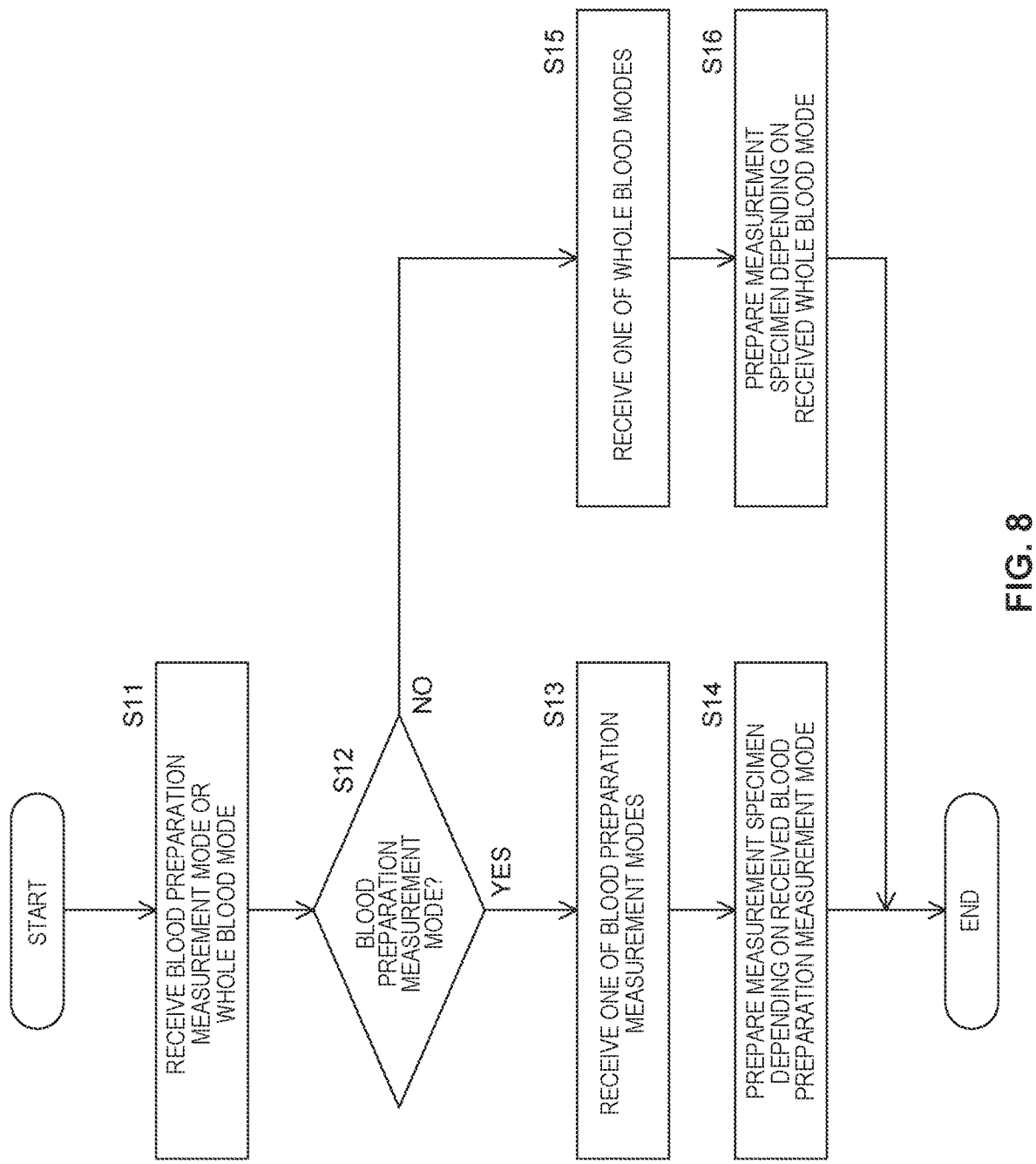

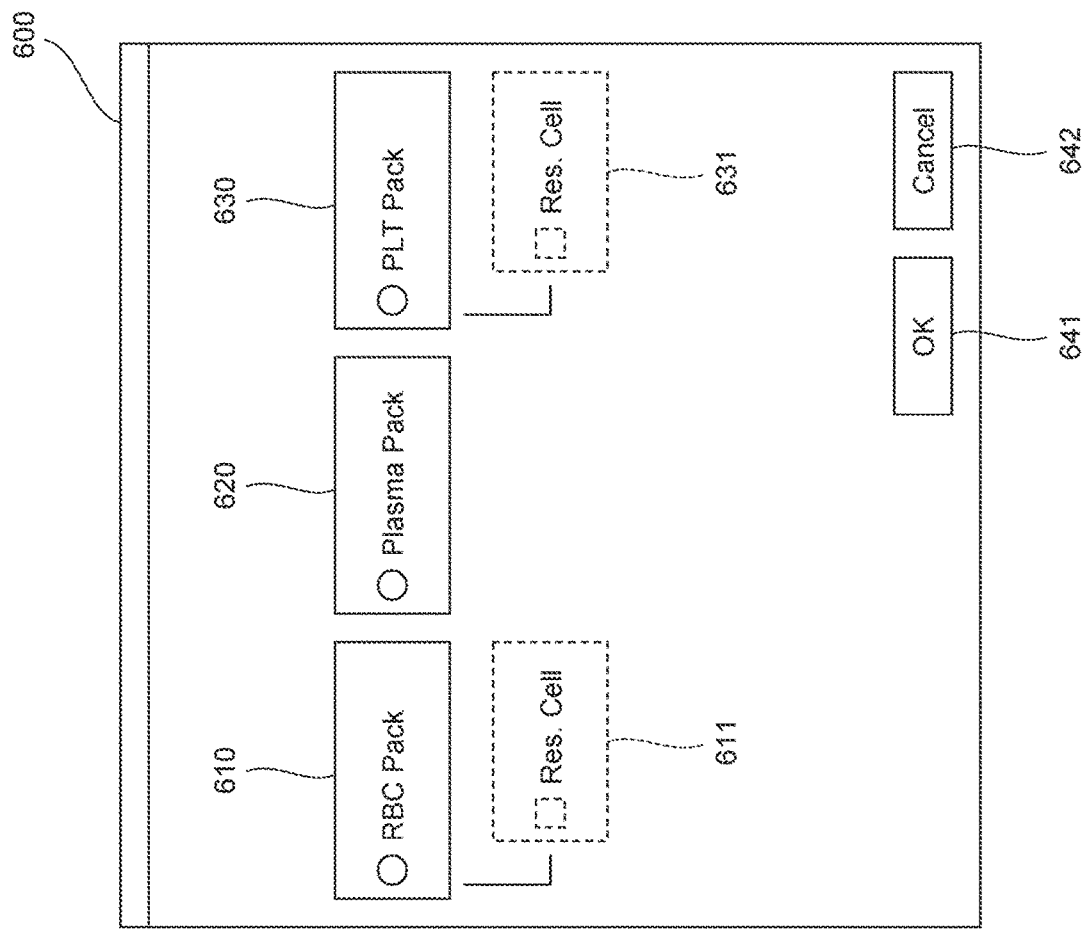

| | MEASUREMENT CHANNEL | | | | |
|---|---|---|---|---|---|
| | RBC/PLT MEASUREMENT | HEMOGLOBIN MEASUREMENT | WHITE BLOOD CELL DIFFERENTIAL MEASUREMENT | RETICULOCYTE COUNT MEASUREMENT | PLATELET COUNT MEASUREMENT (OPTICAL METHOD) |
| STEP S105 RED BLOOD CELL PREPARATION MEASUREMENT MODE | SAME AS WHOLE BLOOD | SAME AS WHOLE BLOOD | — | — | — |
| STEP S106 RED BLOOD CELL PREPARATION + REMAINING BLOOD CELL MEASUREMENT MODE | SAME AS WHOLE BLOOD | SAME AS WHOLE BLOOD | HIGH-SENSITIVITY SETTING | — | — |
| STEP S107 PLASMA PREPARATION MEASUREMENT MODE | — | — | HIGH-SENSITIVITY SETTING | HIGH-SENSITIVITY SETTING | — |
| STEP S108 PLATELET PREPARATION MEASUREMENT MODE | HIGH-SENSITIVITY SETTING | HIGH-SENSITIVITY SETTING | HIGH-SENSITIVITY SETTING | — | SAME AS WHOLE BLOOD |
| STEP S109 PLATELET PREPARATION + REMAINING BLOOD CELL MEASUREMENT MODE | HIGH-SENSITIVITY SETTING | HIGH-SENSITIVITY SETTING | HIGH-SENSITIVITY SETTING | HIGH-SENSITIVITY SETTING | SAME AS WHOLE BLOOD |

FIG. 11

RED BLOOD CELL PREPARATION MEASUREMENT MODE

| MEASUREMENT ITEM | MEASUREMENT CHANNEL |
|---|---|
| RBC | RBC/PLT MEASUREMENT |
| HCT | RBC/PLT MEASUREMENT |
| HGB | HEMOGLOBIN MEASUREMENT |

| REAGENT |
|---|
| CELLPACK DCL |
| SULFOLYSER |

FIG. 12A

RED BLOOD CELL PREPARATION + REMAINING BLOOD CELL MEASUREMENT MODE

| MEASUREMENT ITEM | MEASUREMENT CHANNEL |
|---|---|
| RBC | RBC/PLT MEASUREMENT |
| HCT | RBC/PLT MEASUREMENT |
| HGB | HEMOGLOBIN MEASUREMENT |
| WBC | WHITE BLOOD CELL DIFFERENTIAL MEASUREMENT |

| REAGENT |
|---|
| CELLPACK DCL |
| SULFOLYSER |
| LYSERCELL WDF |
| FLUOROCELL WDF |

FIG. 12B

PLASMA PREPARATION MEASUREMENT MODE

| MEASUREMENT ITEM | MEASUREMENT CHANNEL |
|---|---|
| RBC | RETICULOCYTE COUNT MEASUREMENT |
| WBC | WHITE BLOOD CELL DIFFERENTIAL MEASUREMENT |

| REAGENT |
|---|
| LYSERCELL WDF |
| FLUOROCELL WDF |
| CELLPACK DFL |
| FLUOROCELL RET |

PLATELET PREPARATION MEASUREMENT MODE

| MEASUREMENT ITEM | MEASUREMENT CHANNEL |
|---|---|
| PLT | PLATELET COUNT MEASUREMENT (OPTICAL METHOD) |

| REAGENT |
|---|
| CELLPACK DFL |
| FLUOROCELL PLT |

FIG. 14B

PLATELET PREPARATION + REMAINING BLOOD CELL MEASUREMENT MODE

| MEASUREMENT ITEM | MEASUREMENT CHANNEL |
|---|---|
| PLT | PLATELET COUNT MEASUREMENT (OPTICAL METHOD) |
| RBC | RETICULOCYTE COUNT MEASUREMENT |
| WBC | WHITE BLOOD CELL DIFFERENTIAL MEASUREMENT |

| REAGENT |
|---|
| LYSERCELL WDF |
| FLUOROCELL WDF |
| CELLPACK DFL |
| FLUOROCELL RET |
| FLUOROCELL PLT |

DETERMINATION RESULT: 702 Fail

TAB 710, PLASMA PREPARATION MEASUREMENT MODE

| MEASUREMENT ITEM | DATA | UNIT 712 |
|---|---|---|
| RBC | ..... | 10^4/μL |
| WBC | ..... | 10^2/μL |

TAB 710, PLATELET PREPARATION + REMAINING BLOOD CELL MEASUREMENT MODE

| MEASUREMENT ITEM | DATA | UNIT 711 |
|---|---|---|
| PLT | ..... | 10^4/μL |

| MEASUREMENT ITEM | DATA | UNIT 712 |
|---|---|---|
| RBC | ..... | 10^4/μL |
| WBC | ..... | 10^2/μL |

TAB 720, PLATELET PREPARATION MEASUREMENT MODE

| MEASUREMENT ITEM | DATA | UNIT 721 |
|---|---|---|
| DEGRADED PLATELETS | ..... | 10^4/μL |

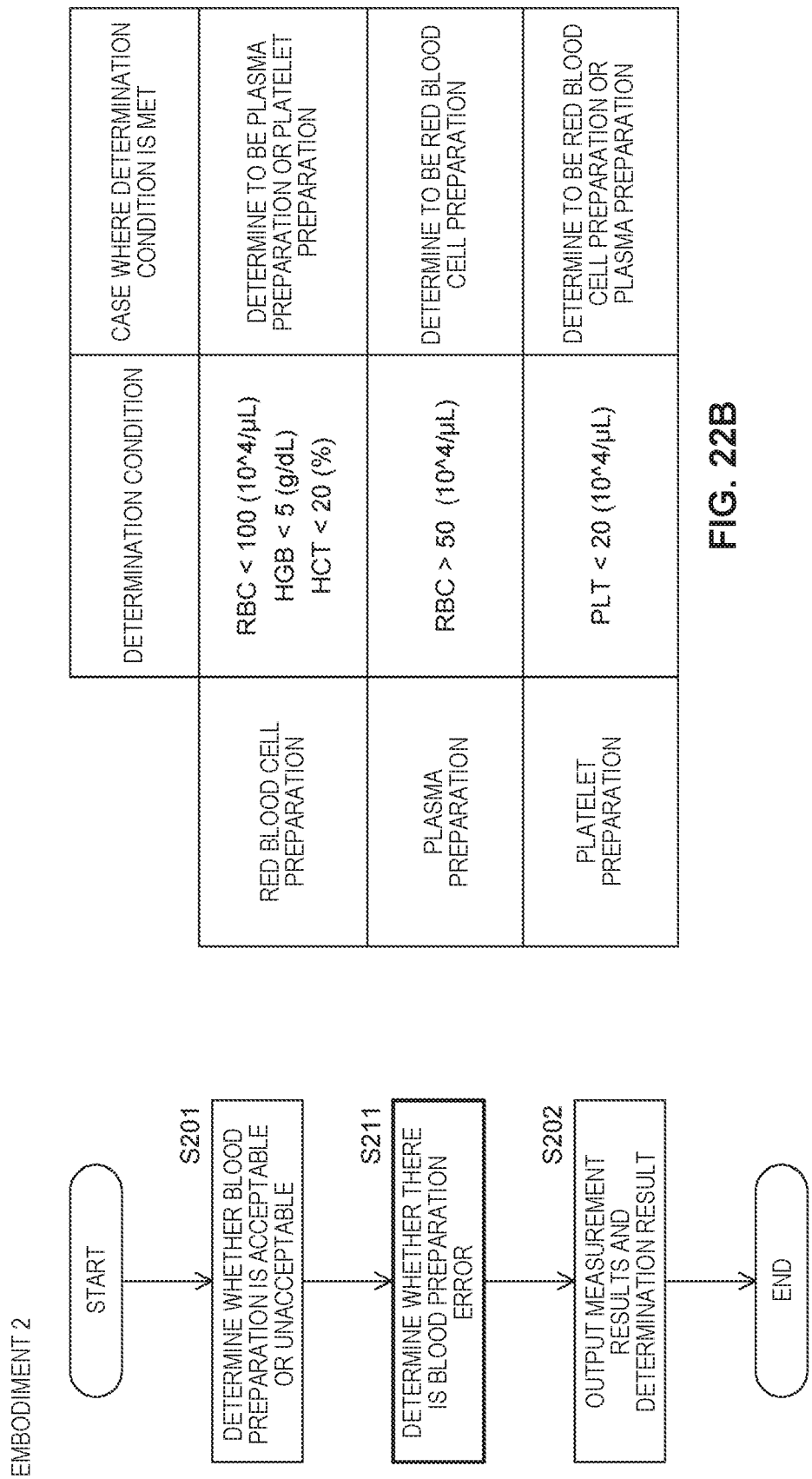

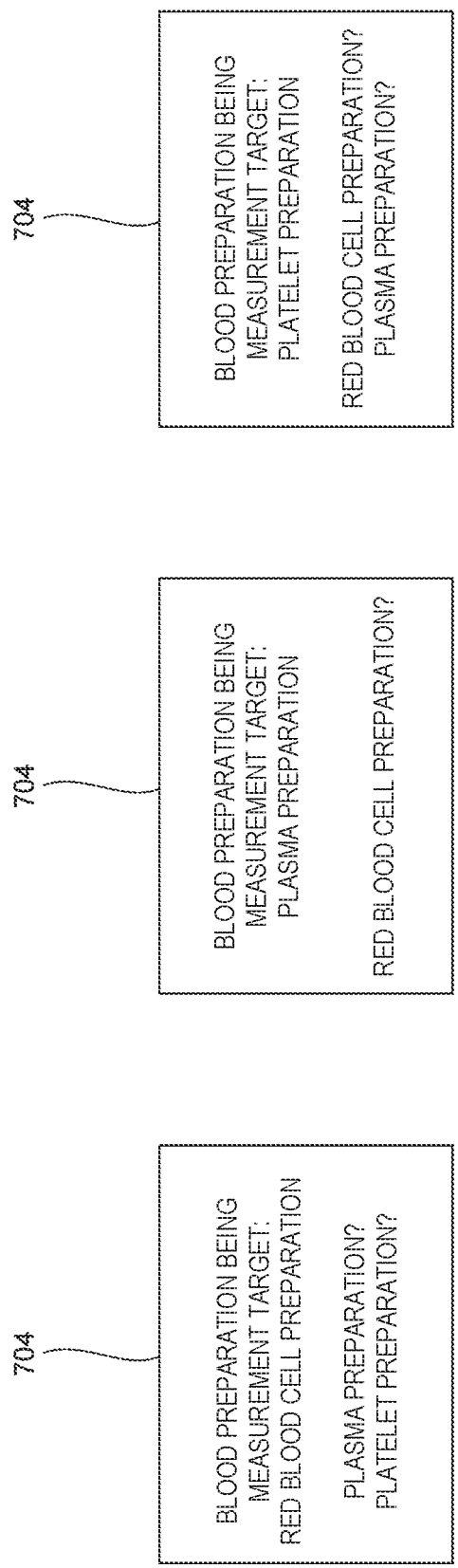

BLOOD ANALYZER, BLOOD ANALYZING METHOD, AND PROGRAM

CROSS REFERENCE TO RELATED APPLICATIONS

This application claims priority from prior Japanese Patent Application No. 2017-155938 filed with the Japan Patent Office on Aug. 10, 2017, the entire contents of which are incorporated herein by reference.

BACKGROUND

The present disclosure relates to a blood analyzer, a blood analyzing method, and a program.

Blood preparations or blood products refer to pharmaceutical products including human blood or substances obtained from human blood as active ingredients. As the blood preparations, there are known component preparations prepared by separating components such as red blood cells, platelets, and plasma from human whole blood or human blood, and blood transfusions are now performed by mainly using the component preparations. The component preparations are used for blood component replacement therapies performed on patients undergoing various surgical operations, patients affected by blood diseases and cancers, and the like. It is known that, when a component preparation is transfused to a patient, white blood cells of a donor remaining in the perpetration cause blood transfusion reactions such as fever and allergic reactions and, in severe cases, cause blood transfusion reactions such as acute lung disorder. Accordingly, prestorage leukoreduction is performed on the component preparation to prevent the blood transfusion reactions. Moreover, since a certain percentage of white blood cells and red blood cells remain in the component preparation, sampling tests for the white blood cell count and red blood cell count are performed before the shipping of the preparation.

Such sampling tests can be performed by using, for example, a flow system (general-purpose flow cytometer) described in Published Japanese Translation of PCT International Application No. 2011-521228 (Patent Literature 1).

When a blood preparation is tested by using a general-purpose flow cytometer like one described above, in order to measure items necessary for blood preparation measurement, an operator needs to perform cumbersome procedures such as manually preparing a measurement specimen for each of the necessary items and individually setting a sensitivity of a detector, a blood cell fractionation method, and the like, before performing the measurement.

In view of such a problem, one or more aspects may provide a blood analyzer, a blood analyzing method, and a program which enable smooth testing of a blood preparation.

SUMMARY

A blood analyzer according to one or more embodiments may include: a specimen preparation part that prepares a measurement specimen by mixing a reagent into a blood preparation; a measurement part that measures the measurement specimen; a measurement mode selection unit that receives an input of a type of blood preparation as a measurement target selected from a plurality of types of blood preparations; and a controller. The controller may cause the specimen preparation part to prepare the measurement specimen depending on the selected type of blood preparation.

A blood analyzing method according to one or more embodiments may include: receiving a type of blood preparation selected from a plurality of types of blood preparation as a measurement target; preparing a measurement specimen based on the received type of blood preparation; and analyzing the prepared measurement specimen.

A non-transitory computer-readable recording medium, according to one or more embodiments, storing a program causing a computer to perform operations may include: receiving a type of blood preparation selected from a plurality of types of blood preparations as a measurement target; preparing a measurement specimen depending on the received type of blood preparation; and analyzing the prepared measurement specimen.

A blood analyzer according to one or more embodiments may include: a specimen preparation part that prepares a measurement specimen by mixing a reagent into a sample, a measurement part that measures the measurement specimen, and a measurement mode selection unit that receives, as a measurement target, an input of one of a blood preparation and whole blood. The specimen preparation part may prepare the measurement specimen depending on the received measurement target.

BRIEF DESCRIPTION OF DRAWINGS

FIG. 2A is a perspective view illustrating a configuration of a container according to an embodiment 1, and FIG. 2B is a perspective view illustrating a configuration of a rack according to an embodiment 1;

FIG. 6A is a diagram schematically illustrating a configuration of an electrical resistance-type detector according to an embodiment 1, FIG. 6B is a diagram schematically illustrating a configuration of a hemoglobin detector according to an embodiment 1, and FIG. 6C is a diagram schematically illustrating a configuration of an optical detector according to an embodiment 1;

FIG. 7 is a diagram illustrating setting of a measurement mode in a blood analyzer according to an embodiment 1;

FIG. 8 is a flowchart illustrating processing of receiving an input of a measurement mode and preparing a measurement specimen depending on a received measurement mode;

FIG. 9A is a diagram illustrating a configuration of a screen for changing a measurement target according to an embodiment 1, and FIG. 9B is a diagram illustrating a configuration of a reception screen for receiving an input of setting of a blood preparation measurement mode according to an embodiment 1;

FIG. 11 is a table illustrating details of setting of measurement processing according to an embodiment 1;

FIG. 12A is a table illustrating measurement items obtained in a red blood cell preparation measurement mode according to an embodiment 1, and FIG. 12B is a table illustrating measurement items obtained in a red blood cell preparation+remaining blood cell measurement mode according to an embodiment 1;

FIG. 13 is a table illustrating measurement items obtained in a plasma preparation measurement mode according to an embodiment 1;

FIG. 14A is a table illustrating measurement items obtained in a platelet preparation measurement mode according to An embodiment 1, and FIG. 14B is a table illustrating measurement items obtained in a platelet preparation+remaining blood cell measurement mode according to an embodiment 1;

FIG. 22A is a flowchart illustrating processing of determining whether a blood preparation is acceptable or not, processing of determining whether there is a blood preparation error, and processing of outputting results according to an embodiment 2, and FIG. 22B is a table illustrating determination standards used in determination of a blood preparation error; and FIGS. 23A to 23C are diagrams illustrating regions displaying information indicating that a blood preparation being a measurement target is a different type of blood preparation according to an embodiment 2.

DETAILED DESCRIPTION

Figure 1:
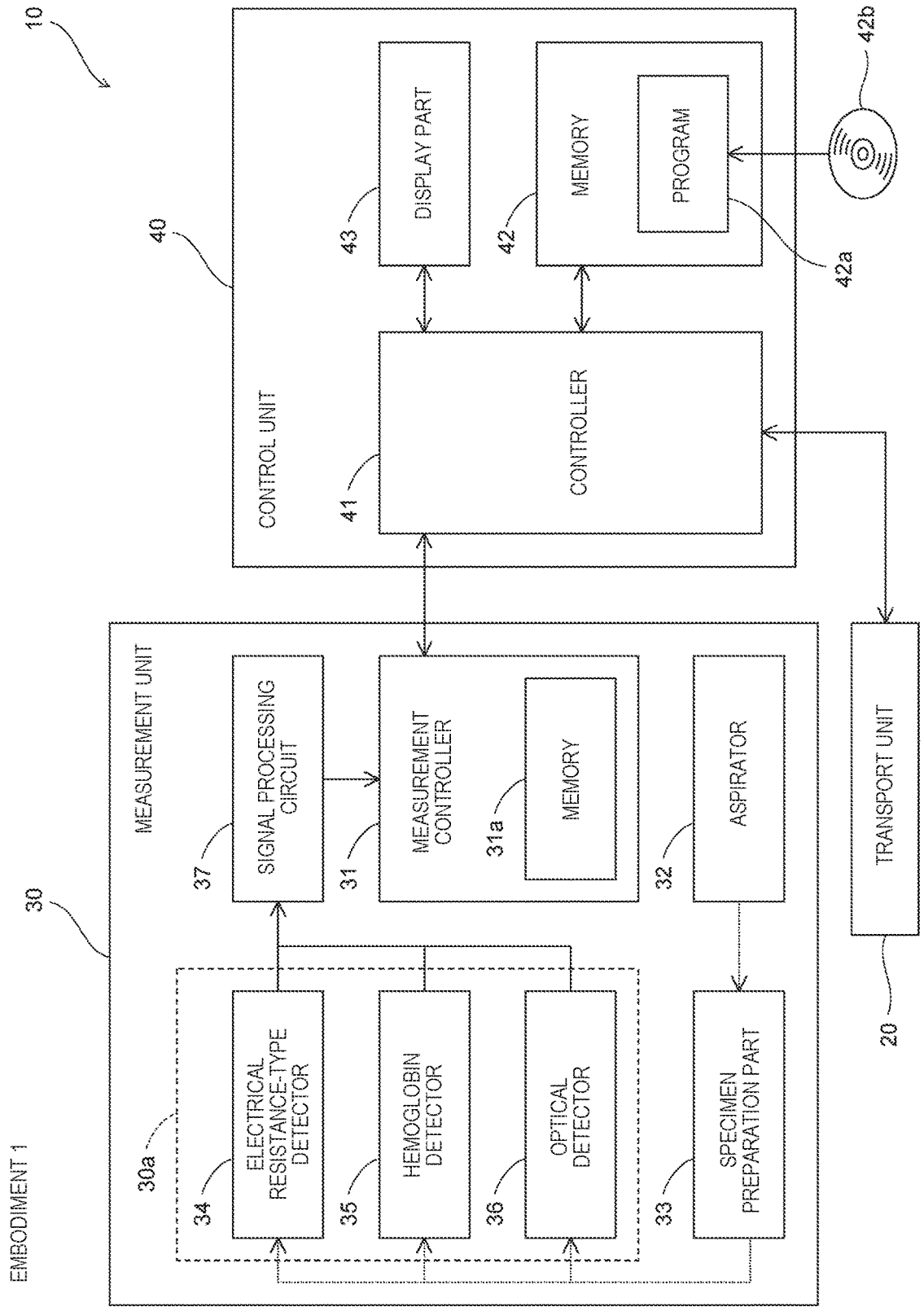
FIG. 1 is a block diagram illustrating a configuration of a blood analyzer according to an embodiment 1.

A first aspect relates to a blood analyzer. A blood analyzer (10) according to the embodiment includes a specimen preparation part (33) that prepares a measurement specimen by mixing a reagent into a blood preparation, a measurement part (30a) that measures the measurement specimen, and a measurement mode selection unit (600) that receives an input of a type of blood preparation to be a measurement target which is selected from types of blood preparations, and prepares the measurement specimen depending on the received type of blood preparation.

The "blood preparation", a blood pack, or a blood product refers to a component preparation prepared by separating a component such as red blood cells, platelets, or plasma from human whole blood or human blood. The blood preparation includes, for example, a red blood cell preparation, a plasma preparation, a platelet preparation, and the like. The "red blood cell preparation", a red blood cell pack, or a red blood cell product refers to a blood preparation prepared by extracting a red blood cell component from the whole blood. The "plasma preparation", a plasma pack, or a plasma product refers to a blood preparation prepared by extracting a plasma component from the whole blood. The "platelet preparation", a platelet pack, or a platelet product refers to a blood preparation prepared by extracting a platelet component from the whole blood. The measurement mode selection unit is configured by buttons on a screen displayed on a display part, a physical button mechanism, or the like. Moreover, the measurement mode selection unit may receive the input on the type of blood preparation from a barcode of a container containing the blood preparation.

The blood analyzer according to the aspect allows an operator to appropriately prepare the measurement specimen depending on the blood preparation being the measurement target only by inputting the type of blood preparation being the measurement target which is selected from the types of blood preparations. Thus, the operator does not have to perform cumbersome procedures such as changing setting according to the type of blood preparation and the like in the measurement of the blood preparation, and the blood preparation can be smoothly tested. Moreover, since the measurement specimen is prepared depending on the blood preparation, it is possible to prevent wasteful consumption of a reagent and reduce the consumption amount of the reagent.

The blood analyzer (10) according to the aspect may be configured such that the measurement mode selection unit (600) is capable of receiving one of at least a red blood cell preparation measurement mode in which the red blood cell preparation is measured and a platelet preparation measurement mode in which the platelet preparation is measured.

The blood analyzer (10) according to the aspect may be configured such that the blood analyzer (10) further includes a display part (43) and the blood analyzer (10) causes the display part (43) to display a reception screen (600) through which to receive the type of blood preparation.

The blood analyzer (10) according to the aspect may be configured to output quality information depending on the type of blood preparation, based on a measurement result of the measurement specimen. The "quality information" includes information indicating whether the quality of the blood preparation is guaranteed or not, a measurement result of a main component of the blood preparation, a count result of blood cells remaining in the blood preparation, and the like. The quality information is outputted, for example, by being displayed on the display part provided in the blood analyzer, by being sent to a device other than the blood analyzer, by being outputted from a speaker provided in the blood analyzer by means of audio, or by other similar methods. This causes the quality information depending on the type of blood preparation to be outputted, and the operator can thus easily and appropriately perform the quality test of the blood preparation.

In this case, the blood analyzer (10) according to the aspect may be configured to determine whether the blood preparation is acceptable or not, based on a standard for blood component depending on the received type of blood preparation and the measurement result of the measurement specimen prepared from the blood preparation.

The blood analyzer (10) according to the aspect may be configured to output the standard for blood component depending on the received type of blood preparation and the measurement result of the measurement specimen prepared from the blood preparation. The operator can thereby determine the quality of the blood preparation by referring to the outputted standard and the outputted measurement result.

The blood analyzer (10) according to the aspect may be configured such that the types of blood preparations include the red blood cell preparation and, when receiving the red blood cell preparation as the measurement target, the blood analyzer (10) according to the aspect controls the measurement part (30a) such that the measurement part (30a) measures a red blood cell count in the red blood cell preparation. The operator can thereby measure the red blood cell count in the red blood cell preparation only by inputting the red blood cell preparation.

The blood analyzer (10) according to the aspect may be configured such that the types of blood preparations include the red blood cell preparation and, when receiving the red blood cell preparation as the measurement target, the blood analyzer (10) according to the aspect controls the measurement part (30a) such that the measurement part (30a) measures a white blood cell count in the red blood cell preparation. The operator can thereby measure the count of white blood cells to be removed in the red blood cell preparation only by inputting the red blood cell preparation.

In this case, the blood analyzer (10) according to the aspect may be configured to determine whether the red blood cell preparation is acceptable or not based on a standard for white blood cell count and the measured white blood cell count.

The blood analyzer (10) according to the aspect may be configured such that the types of blood preparations include the platelet preparation and, when receiving the platelet preparation as the measurement target, the blood analyzer (10) according to the aspect controls the measurement part (30a) such that the measurement part (30a) measures a platelet count in the platelet preparation. The operator can thereby measure the platelet count in the platelet preparation only by inputting the platelet preparation.

The blood analyzer (10) according to the aspect may be configured such that the types of blood preparations include the platelet preparation and, when receiving the platelet preparation as the measurement target, the blood analyzer (10) according to the aspect controls the measurement part (30a) such that the measurement part (30a) measures the white blood cell count in the platelet preparation. The operator can thereby measure the count of white blood cells to be removed in the platelet preparation only by inputting the platelet preparation.

In this case, the blood analyzer (10) according to the aspect may be configured to determine whether the platelet preparation is acceptable or not based on the standard for white blood cell count and the measured white blood cell count.

The blood analyzer (10) according to the aspect may be configured such that the types of blood preparations include a platelet preparation and, when receiving the platelet preparation as the measurement target, the blood analyzer (10) according to the aspect controls the measurement part (30a) such that the measurement part (30a) measures the red blood cell count in the platelet preparation. The operator can thereby measure the count of red blood cells to be removed in the platelet preparation only by inputting the platelet preparation.

In this case, the blood analyzer (10) according to the aspect may be configured to determine whether the platelet preparation is acceptable or not based on the standard for red blood cell count and the measured red blood cell count.

The blood analyzer (10) according to the aspect may be configured to control the measurement part (30a) such that the measurement part (30a) measures a fluorescence intensity of particles in the platelet preparation and to determine whether the platelet preparation is acceptable or not, based on the number of particles with a lower fluorescence intensity than a fluorescence intensity of platelets. The particles with the lower fluorescence intensity in the platelet preparation are considered to be degraded platelets. Accordingly, whether the platelet preparation is acceptable or not can be determined based on the number of particles with the lower fluorescence intensity than the fluorescence intensity of the platelets.

In this case, the blood analyzer (10) according to the aspect may be configured to determine whether the platelet preparation is acceptable or not based on a standard for the number of particles with the lower fluorescence intensity in the platelet preparation and the measured number of particles with the lower fluorescence intensity in the platelet preparation.

The blood analyzer (10) according to the aspect may be configured such that the types of blood preparations include the plasma preparation and, when receiving the plasma preparation as the measurement target, the blood analyzer (10) according to the aspect controls the measurement part (30a) such that the measurement part (30a) measures the white blood cell count in the plasma preparation. The operator can thereby measure the count of white blood cells to be removed in the plasma preparation only by inputting the plasma preparation.

In this case, the blood analyzer (10) according to the aspect may be configured to determine whether the plasma preparation is acceptable or not based on the standard for white blood cell count and the measured white blood cell count.

The blood analyzer (10) according to the aspect may be configured such that the types of blood preparations include a plasma preparation and, when receiving the plasma preparation as the measurement target, the blood analyzer (10) according to the aspect controls the measurement part (30a) such that the measurement part (30a) measures the red blood cell count in the plasma preparation. The operator can thereby measure the count of red blood cells to be removed in the plasma preparation only by inputting the plasma preparation.

In this case, the blood analyzer (10) according to the aspect may be configured to determine whether the plasma preparation is acceptable or not based on the standard for red blood cell count and the measured red blood cell count.

The blood analyzer (10) according to the aspect may further include an agitator (310) that agitates the blood preparation, and be configured to control the agitator (310) such that an intensity of agitating the blood preparation is changed depending on the received type of blood preparation.

The blood analyzer (10) according to the aspect may further include the agitator (310) that agitates the blood preparation and be configured such that the types of blood preparations include the red blood cell preparation and the platelet preparation and the blood analyzer (10) according to the aspect controls the agitator (310) such that an intensity of agitation by the agitator (310) in the case where the blood analyzer (10) receives the red blood cell preparation as the measurement target is higher than an intensity of agitation by the agitator (310) in the case where the blood analyzer (10) receives the platelet preparation as the measurement target.

The viscosity of the red blood cell preparation is higher than that of the platelet preparation. Thus, when the agitation of the red blood cell preparation is insufficient, there is a risk that the red blood cells in the red blood cell preparation are not evenly mixed and the red blood cell preparation cannot be accurately measured. Accordingly, setting the intensity of agitation for the red blood cell preparation higher than that for the platelet preparation can improve the measurement accuracy of the red blood cell preparation. Moreover, excessive agitation of the platelet preparation may give a false high reading for the count of white blood cells remaining in the platelet preparation. Accordingly, setting the intensity of agitation for the platelet preparation lower than that for the red blood cell preparation can suppress the false high reading of the white blood cell count.

The blood analyzer (10) according to the aspect may further include the agitator (310) that agitates the blood preparation and be configured such that the types of blood preparations include the red blood cell preparation and the plasma preparation and the blood analyzer (10) according to the aspect controls the agitator (310) such that an intensity of agitation by the agitator (310) in the case where the blood analyzer (10) receives the red blood cell preparation as the measurement target is higher than an intensity of agitation by the agitator (310) in the case where the blood analyzer (10) receives the plasma preparation as the measurement target.

The viscosity of the red blood cell preparation is higher than that of the plasma preparation. Thus, when the agitation of the red blood cell preparation is insufficient, there is a risk that the red blood cells in the red blood cell preparation are not evenly mixed and the red blood cell preparation cannot be accurately measured. Accordingly, setting the intensity of agitation for the red blood cell preparation higher than that for the plasma preparation can improve the measurement accuracy of the red blood cell preparation. Moreover, excessive agitation of the plasma preparation may give a false high reading for the count of white blood cells remaining in the plasma preparation. Accordingly, setting the intensity of agitation for the plasma preparation lower than that for the red blood cell preparation can suppress the false high reading of the white blood cell count.

The blood analyzer (10) according to the aspect may be configured such that the types of blood preparations include the red blood cell preparation and the platelet preparation and the blood analyzer (10) according to the aspect controls the measurement part (30*a*) such that the measurement part (30*a*) measures the measurement specimen with an electrical resistance-type detector (34) when the blood analyzer (10) receives the red blood cell preparation as the measurement target, and measures the measurement specimen with an optical detector (36) when the blood analyzer (10) receives the platelet preparation as the measurement target.

The blood analyzer (10) according to the aspect may be configures such that the types of blood preparations include the red blood cell preparation and the platelet preparation and the blood analyzer (10) according to the aspect controls the measurement part (30*a*) such that a detection sensitivity of the red blood cell count in the case where the blood analyzer (10) receives the platelet preparation as the measurement target is higher than a detection sensitivity of the red blood cell count in the case where the blood analyzer (10) receives the red blood cell preparation as the measurement target. The red blood cell count in the red blood cell preparation and the count of red blood cells remaining in the platelet preparation can be thereby appropriately measured.

In this case, the blood analyzer (10) according to the aspect may be configured such that, when receiving the platelet preparation as the measurement target, the blood analyzer (10) controls the specimen preparation part (33) such that the specimen preparation part (33) mixes the platelet preparation with a reagent for measuring reticulocytes to prepare the measurement specimen. This enables accurate measurement of the count of very few red blood cells remaining in the platelet preparation.

The blood analyzer (10) according to the aspect may be configured such that the types of blood preparations include the red blood cell preparation and the plasma preparation and the blood analyzer (10) according to the aspect controls the measurement part (30*a*) such that the measurement part (30*a*) measures the measurement specimen with the electrical resistance-type detector (34) when the blood analyzer (10) receives the red blood cell preparation as the measurement target, and measures the measurement specimen with the optical detector (36) when the blood analyzer (10) receives the plasma preparation as the measurement target.

The blood analyzer (10) according to the aspect may be configured such that the types of blood preparations include the red blood cell preparation and the plasma preparation and the blood analyzer (10) according to the aspect controls the measurement part (30*a*) such that a detection sensitivity of the red blood cell count in the case where the blood analyzer (10) receives the plasma preparation as the measurement target is higher than a detection sensitivity of the red blood cell count in the case where the blood analyzer (10) receives the red blood cell preparation as the measurement target. The red blood cell count in the red blood cell preparation and the count of red blood cells remaining in the plasma preparation can be thereby appropriately measured.

In this case, the blood analyzer (10) according to the aspect may be configured such that, when receiving the plasma preparation as the measurement target, the blood analyzer (10) controls the specimen preparation part (33) such that the specimen preparation part (33) mixes the plasma preparation with a reagent for measuring reticulocytes to prepare the measurement specimen. This enables accurate measurement of the count of very few red blood cells remaining in the plasma preparation.

The blood analyzer (10) according to the aspect may be configured such that the blood analyzer (10) is capable of receiving whole blood as the measurement target and, when receiving the whole blood as the measurement target, controls the measurement part (30*a*) such that the measurement part (30*a*) measures the white blood cell count in the measurement specimen. This allows the operator to analyze both of the blood preparation and the whole blood by using one blood analyzer, and there is no need to separately measure the blood preparation and the whole blood by using devices.

In this case, the blood analyzer (10) according to the aspect may be configured to control the measurement part (30*a*) such that the amount of measurement specimen measured in the white blood cell count measurement performed when the blood analyzer (10) receives the blood preparation as the measurement target is larger than the amount of measurement specimen measured in the white blood cell count measurement performed when the blood analyzer (10) receives the whole blood as the measurement target.

The blood analyzer (10) according to the aspect may be configured to further include a controller (41) that controls the specimen preparation part (33) such that the specimen preparation part (33) prepares the measurement specimen depending on the received type of blood preparation.

A second aspect relates to a blood analyzing method. In the blood analyzing method according to the aspect, one of types of blood preparations is received as a measurement target, a measurement specimen is prepared depending on the received type of blood preparation, and the prepared measurement specimen is analyzed.

In the blood analyzing method according to the aspect, effects similar to those of the first aspect are obtained.

A third aspect relates to a program. The program (42a) according to the aspect causes a computer to execute processing of receiving one of types of blood preparations as a measurement target, processing of preparing a measurement specimen depending on the received type of blood preparation, and processing of analyzing the prepared measurement specimen.

In the program according to the aspect, effects similar to those of the first aspect are obtained.

A fourth aspect relates to a blood analyzer. The blood analyzer (10) according to the aspect includes the specimen preparation part (33) that mixes a reagent into a sample to prepare a measurement specimen, and the measurement part (30a) that measures the measurement specimen, the measurement mode selection unit that receives one of a blood preparation or whole blood as a measurement target, and prepares the measurement specimen depending on the received measurement target.

In the blood analyzer according to the aspect, the operator can analyze both of the blood preparation and the whole blood by using one blood analyzer. Accordingly, there is no need to separately measure the blood preparation and the whole blood by using devices.

One or more aspects may enable smooth testing of a blood preparation.

Embodiment 1

An embodiment 1 described below is an embodiment in which one or more aspects are applied to a blood analyzer that analyzes samples such as blood collected from a subject. In the blood analyzer of an embodiment 1, measurement targets are mainly whole blood and blood preparation. Although the blood analyzer of an embodiment 1 can measure samples other than the whole blood such as body fluids, description is given below of the case where the measurement targets are the whole blood and the blood preparation for the sake of convenience.

When the measurement target is the whole blood, one of whole blood modes for the whole blood is set and, when the measurement target is the blood preparation, one of blood preparation measurement modes for the blood preparation is set. In the whole blood modes, the whole blood is measured and, in the blood preparation measurement modes, the blood preparation is measured. Here, the blood preparation refers to a component preparation prepared by separating a component such as red blood cells, platelets, or plasma from human whole blood or human blood. Types of blood preparations in an embodiment 1 include a red blood cell preparation, a plasma preparation, and a platelet preparation. The red blood cell preparation refers to a blood preparation prepared by extracting a red blood cell component from the whole blood. The plasma preparation refers to a blood preparation prepared by extracting a plasma component from the whole blood. The platelet preparation refers to a blood preparation prepared by extracting a platelet component from the whole blood.

As illustrated in FIG. 1, the blood analyzer 10 includes a transport unit 20, a measurement unit 30, and a control unit 40.

The transport unit 20 is configured to be capable of transporting a rack 120 illustrated in FIG. 2B. Containers 110 illustrated in FIG. 2A are held in the rack 120. The transport unit 20 transports the rack 120 to supply the containers 110 held in the rack 120 to the measurement unit 30. An operation of the transport unit 20 transporting the rack 120 to supply the containers 110 to the measurement unit 30 as described above is hereafter referred to as "sampler operation." The transport unit 20 is connected to be communicable with the control unit 40 and is controlled by the control unit 40. The configuration of the transport unit 20 is described later with reference to FIG. 3.

As illustrated in FIG. 2A, each of the containers 110 includes a body portion 111, a cap portion 112, and a barcode label 113. The body portion 111 may be a tubular container made of a transparent glass or synthetic resin and hold the sample or the blood preparation. The cap portion 112 may be made of rubber and is configured to tightly seal an opening at an upper end of the body portion 111. The barcode label 113 is attached to a side surface of the body portion 111. A barcode indicating a sample ID or a blood preparation ID is printed on the barcode label 113. The sample ID is information which makes the samples individually distinguishable. The blood preparation ID is information which makes the blood preparations individually distinguishable.

As illustrated in FIG. 2B, the rack 120 includes ten holders 121 and a barcode label 122. The holders 121 are configured to be capable of holding the containers 110 in a vertical position. The barcode label 122 is attached to a side surface of the rack 120. A barcode indicating a rack ID is printed on the barcode label 122. The rack ID is information which makes the racks 120 individually distinguishable.

Returning to FIG. 1, the measurement unit 30 includes a measurement controller 31, an aspirator 32, a specimen preparation part 33, a measurement part 30a, and a signal processing circuit 37.

The measurement controller 31 is configured by, for example, a CPU, a MPU, and the like. The measurement controller 31 receives signals outputted by the parts of the measurement unit 30 and controls the parts of the measurement unit 30. The measurement controller 31 communicates with the control unit 40. The measurement controller 31 includes a memory 31a. The memory 31a is configured by, for example, a ROM, a RAM, a hard disk drive, and the like. The measurement controller 31 performs various types of processing based on a program stored in the memory 31a.

Figure 3:
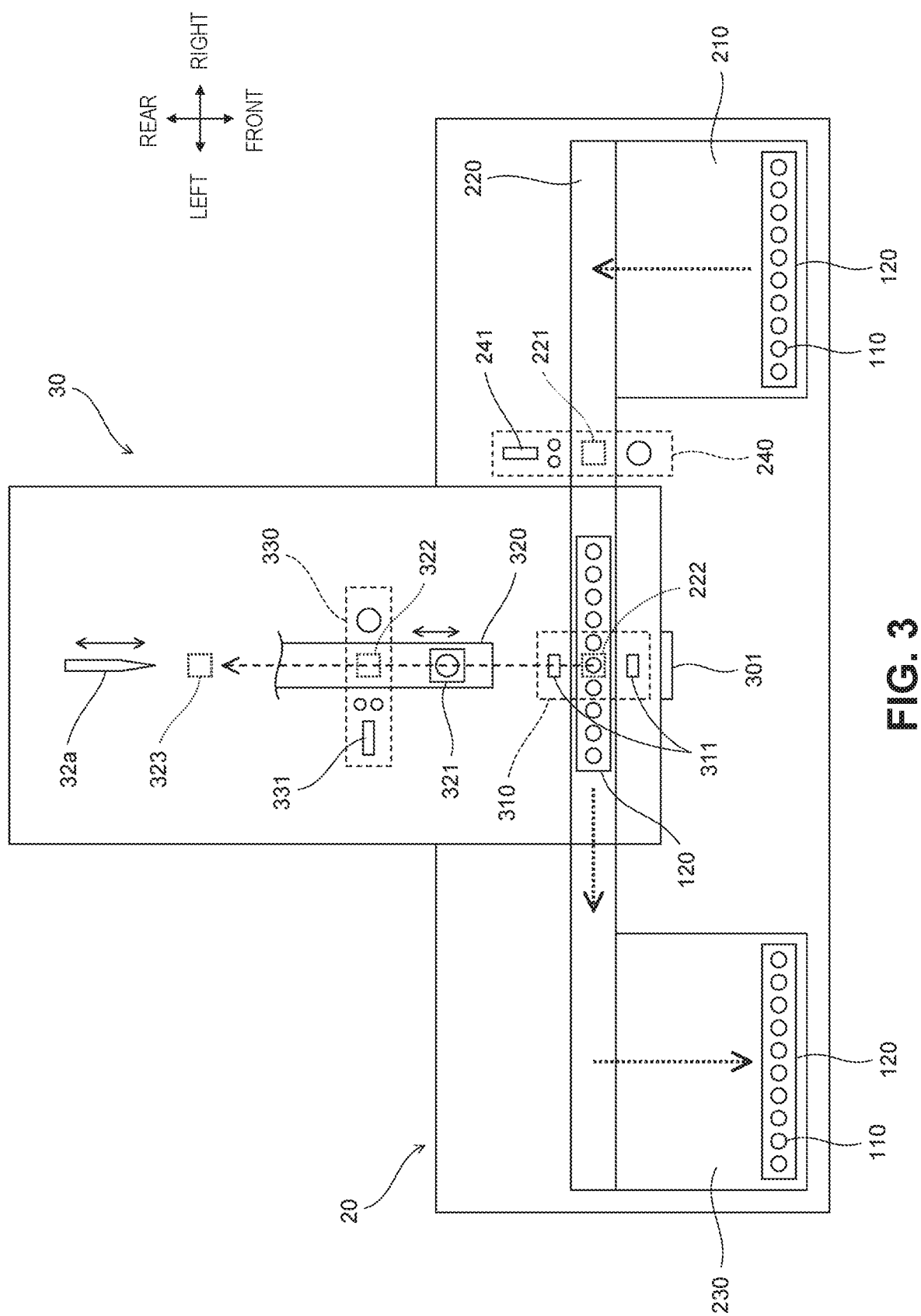
FIG. 3 is a diagram schematically illustrating configurations of a transport unit and a measurement unit according to an embodiment 1.

The aspirator 32 includes an aspiration tube 32a illustrated in FIG. 3 and aspirates the samples and the blood preparations from the containers 110 supplied to the measurement unit 30, by using the aspiration tube 32a. Note that the containers 110 are not only supplied to the measurement unit 30 by the transport unit 20 in the aforementioned sampler operation but also manually supplied to the measurement unit 30 by an operator. An operation of the operator directly supplying the containers 110 to the measurement unit 30 as described above is hereafter referred to as "manual operation." The operator can set the operation of supplying the containers 110 to the measurement unit 30 to either the sampler operation or the manual operation by operating a menu or the like displayed on a display part 43.

Containers respectively holding reagents to be used for the measurement are connected to the specimen preparation part 33. In the measurement of samples, the specimen preparation part 33 prepares measurement specimens by mixing the samples aspirated by the aspirator 32 with the reagents. In the measurement of blood preparations, the specimen preparation part 33 prepares measurement specimens by mixing the blood preparations aspirated by the aspirator 32 with the reagents. The specimen preparation part 33 prepares each of a red blood cell count/platelet count measurement specimen (electrical resistance method), a hemoglobin measurement specimen, a white blood cell count measurement specimen, a white blood cell differential measurement specimen, a reticulocyte count measurement specimen, and a platelet count measurement specimen (optical method) by mixing a sample or a blood preparation with a predetermined reagent. For the sake of convenience, the red blood cell count/platelet count measurement specimen (electrical resistance method) is hereafter referred to as "RBC/PLT measurement specimen." The reagents connected to the specimen preparation part 33 and the measurement specimens prepared by the specimen preparation part 33 are described later with reference to FIG. 5.

The measurement part 30*a* measures the measurement specimens prepared by the specimen preparation part 33. The measurement part 30*a* includes an electrical resistance-type detector 34, a hemoglobin detector 35, and an optical detector 36. These detectors measure the measurement specimens described above.

Specifically, the electrical resistance-type detector 34 measures blood cells based on the RBC/PLT measurement specimen by using a sheath flow DC detection method. The hemoglobin detector 35 measures hemoglobin based on the hemoglobin measurement specimen by using a SLS-hemoglobin method. The optical detector 36 measures blood cells based on the white blood cell count measurement specimen, the white blood cell differential measurement specimen, the reticulocyte count measurement specimen, and the platelet count measurement specimen (optical method) by using a flow cytometry method. The configurations of the electrical resistance-type detector 34, the hemoglobin detector 35, and the optical detector 36 are described later with reference to FIGS. 6A to 6C, respectively.

The signal processing circuit 37 extracts a waveform corresponding to particles based on a detection signal outputted from the electrical resistance-type detector 34 and calculates the peak value of the waveform for each particle. The signal processing circuit 37 calculates a hemoglobin concentration based on a detection signal outputted from the hemoglobin detector 35. The signal processing circuit 37 extracts a waveform corresponding to the particles based on a detection signal outputted from the optical detector 36 and calculates the peak value, width, area, and the like of the waveform for each particle. The signal processing circuit 37 performs the aforementioned signal processing on the detection signals outputted from the electrical resistance-type detector 34, the hemoglobin detector 35, and the optical detector 36 to generate measurement data and outputs the generated measurement data to the measurement controller 31.

The measurement controller 31 stores the measurement data outputted from the signal processing circuit 37 in the memory 31*a*. When the measurement of one sample or one blood preparation is completed, the measurement controller 31 sends the measurement data stored in the memory 31*a* to the control unit 40.

The control unit 40 includes a controller 41, a memory 42, and the display part 43.

The controller 41 is configured by, for example, a CPU. The controller 41 receives signals outputted by the parts of the control unit 40 and controls the parts of the control unit 40. The controller 41 communicates with the transport unit 20 to control the transport unit 20. The controller 41 communicates with the measurement controller 31 of the measurement unit 30 to control the parts of the measurement unit 30 via the measurement controller 31. The controller 41 stores the measurement data received from the measurement unit 30 in the memory 42. The controller 41 analyzes each of the samples by using the measurement data based on the sample and obtains resultant values of measurement items, as the measurement results. Moreover, the controller 41 performs analysis based on each of the blood preparations by using the measurement data based on the blood preparation and obtains resultant values of measurement items, as the measurement results.

Note that the measurement unit 30 and the control unit 40 may be configured to be an integral unit. In this case, for example, the measurement controller 31 is omitted and the controller 41 controls the parts of the measurement unit 30 and the control unit 40.

The memory 42 is configured by, for example, a ROM, a RAM, a hard disk drive, and the like. The controller 41 performs various types of processing based on a program 42*a* stored in the memory 42. The processing of the controller 41 to be described later with reference to the flowcharts is performed based on the program 42*a*. The program 42*a* is not limited to be stored in advance in the memory 42 and may be copied or installed from a storage medium 42*b* via a not-illustrated reading device provided in the control unit 40. The storage medium 42*b* is configured by, for example, an optical disc such as a CD-ROM. Moreover, the program 42*a* may be copied or installed from another computer via a communication cable or the like.

The display part 43 displays an image and receives inputs from the operator. The display part 43 is configured by, for example, a touch panel display. The control unit 40 may separately include, instead of the display part 43, a display part for displaying an image and an input part for receiving inputs from the operator.

Here, the controller 41 measures and analyzes the blood preparation in the blood preparation measurement mode by executing the program 42*a*. In this case, the controller 41 receives an input of one of the blood preparation measurement modes for the blood preparation from the operator via the display part 43. The input of the blood preparation measurement mode is performed through a reception screen 600 to be described later with reference to FIG. 9B. The blood preparation measurement modes are described later with reference to FIG. 7. Next, the controller 41 controls the specimen preparation part 33 such that the specimen preparation part 33 prepares the measurement specimen by using the reagent corresponding to the inputted blood preparation measurement mode, and controls the measurement part 30*a* such that the measurement part 30*a* measures the measurement specimen depending on the inputted blood preparation measurement mode.

As described above, the operator can appropriately measure the blood preparation being the measurement target only by inputting one of the blood preparation measurement modes which corresponds to the measurement to be executed. The operator thereby does not have to perform complex procedures such as changing settings depending on the blood preparation and the like in the measurement of the blood preparation. Accordingly, the blood preparation can be smoothly tested. Moreover, since the measurement specimen is prepared depending on the blood preparation, it is possible to prevent wasteful consumption of the reagents and reduce the consumption amount of the reagents.

Next, transport of the containers 110 is described with reference to FIG. 3.

The transport unit 20 includes a storage portion 210, a transporter 220, a storage portion 230, and a barcode unit 240. The measurement unit 30 includes, in addition to the configuration illustrated in FIG. 1, an agitator 310, a container transporter 320, and a barcode unit 330. Note that, as described above, the transport unit 20 is used in the sampler operation.

The storage portion 210 stores the unprocessed rack 120. The transporter 220 receives the rack 120 transported rearward in the storage portion 210 and transports the received rack 120 leftward. The barcode unit 240 rotates the container 110, located at a read position 221 on the transporter 220, in the holder 121 and reads the sample ID or the preparation ID from the barcode label 113 of the container 110 by using a barcode reader 241. Moreover, the barcode unit 240 reads the rack ID from the barcode label 122 of the rack 120 located at the read position 221.

The agitator 310 includes a pair of grippers 311 for holding the container 110 therebetween from the front side and the rear side. The agitator 310 grips the container 110 located at a take-out position 222 on the transporter 220, by using the grippers 311. The agitator 310 moves the grippers 311 upward while holding the container 110 between the grippers 311 and thereby takes out the container 110 held in the rack 120 from the holder 121. Then, the agitator 310 agitates the sample or the blood preparation in the container 110 by turning the grippers 311 at a position above the rack 120, after which the container 110 is installed in the holder 321 of the container transporter 320 for transport to positions for further processing, including aspirating the sample or the blood preparation from the container 110 and mixing the sample or the blood preparation with reagents as is described in greater detail hereinafter. For example, the container 110 agitated by the agitator 310 may be installed in the holder 321 of the container transporter 320 as discussed in greater detail hereafter.

Figure 4B:
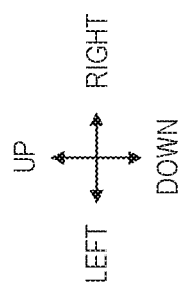
FIG. 4B is a table describing the numbers of times an agitator turns over a container according to an embodiment 1.
Figure 4A:
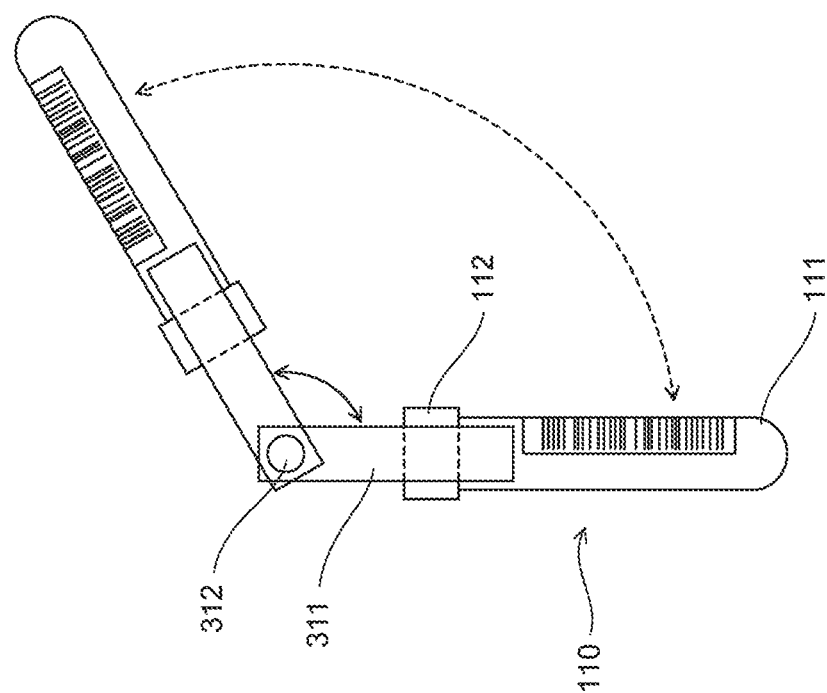
FIG. 4A is a diagram schematically illustrating agitation of a container by an agitator according to an embodiment 1.

As illustrated in FIG. 4A, the grippers 311 are installed on a shaft 312 extending in the front-rear direction to be turnable about the shaft 312. The controller 41 controls the agitator 310 via the measurement controller 31 and turns the grippers 311 gripping the container 110 about the shaft 312. As illustrated by the broken line in FIG. 4A, the container 110 is thereby turned and the sample or the blood preparation in the container 110 is agitated.

When agitating the liquid in the container 110 by using the agitator 310, the controller 41 changes the intensity of the agitation depending on the type of liquid in the container 110. Specifically, the intensity of agitation is defined based on the number of times of performing a turn over operation, which is an operation of moving the container 110 from a standing state to a turned over state and then back to the standing state as illustrated in FIG. 4A. Moreover, the intensity of agitation is also defined based on the angle at which the container 110 is tilted in the turn over operation and the time in which the container 110 is kept in the turned over state in the turn over operation.

As illustrated in FIG. 4B, when the liquid in the container 110 is the whole blood or the red blood cell preparation, the controller 41 performs the turn over operation eight times. When the liquid in the container 110 is the plasma preparation or the platelet preparation, the controller 41 performs the turn over operation five times. Specifically, the controller 41 performs the turn over operation eight times in the whole blood modes. The controller 41 performs the turn over operation eight times in a red blood cell preparation measurement mode and a red blood cell preparation+remaining blood cell measurement mode. The controller 41 performs the turn over operation five times in a plasma preparation measurement mode. The controller 41 performs the turn over operation five times in a platelet preparation measurement mode and a platelet preparation+remaining blood cell measurement mode. The measurement modes are described later with reference to FIG. 7. Moreover, although the number of times of turn over is eight for both of the whole blood and the red blood cell preparation, the turn over angle and the time kept in the turned over state for the red blood cell preparation are greater than the turn over angle and the time kept in the turned over state for the whole blood.

As described above, the intensity of agitation for the red blood cell preparation is greater than the intensities of agitation for the whole blood, the plasma preparation, and the platelet preparation. Moreover, the intensities of agitation for the plasma preparation and the platelet preparation are smaller than the intensities of agitation for the whole blood and the red blood cell preparation.

The viscosity of the red blood cell preparation is higher than those of the whole blood, the plasma preparation, and the platelet preparation. Thus, when the agitation of the red blood cell preparation is insufficient, there is a risk that the red blood cells in the red blood cell preparation do not evenly mix and the red blood cell preparation cannot be accurately measured. Accordingly, setting the intensity of agitation for the red blood cell preparation higher than those for the whole blood, the plasma preparation, and the platelet preparation can improve the measurement accuracy of the red blood cell preparation. Moreover, excessive agitation of the plasma preparation and the platelet preparation may give a false high reading for the count of white blood cells remaining in these preparations, due to an effect of an artifact. Accordingly, setting the intensity of agitation for the plasma preparation and the platelet preparation lower than those for the whole blood and the red blood cell preparation can suppress the false high reading of the white blood cell count.

Moreover, as described above, since the blood preparations and the whole blood vary in characteristics, the number of times of turn over operation by the agitator 310 in some of the blood preparation measurement modes is changed from that in the whole blood mode. This enables accurate measurement of the blood preparations and the whole blood.

Note that matters defining the intensity of agitation are not limited to the number of times of turn over operation, the turn over angle, and the time kept in the turned over state. For example, the intensity of agitation may be defined by turn over speed in the turn over operation. Moreover, the agitation of liquid in the container 110 is not limited to agitation performed by turning the container 110 gripped by the grippers 311 about the shaft 312 as illustrated in FIG. 4A. For example, the agitation of liquid in the container 110 may be performed by shaking the container 110 in an up-down direction or a left-right direction or by shaking the rack 120 holding the container 110. In this case, the intensity of agitation is defined by, for example, the number of times of shaking the container 110 and the speed of shaking.

Returning to FIG. 3, the container transporter 320 includes a holder 321 that can hold the container 110 in a vertical position and a mechanism for transferring the holder 321 in the front-rear direction. The container 110 which is taken out from the rack 120 and the liquid in which is agitated is installed in the holder 321 of the container transporter 320. The container 110 installed in the holder 321 is transferred rearward by the drive of the holder 321. The barcode unit 330 rotates the container 110, located at a read position 322, in the holder 321 to read the sample ID or the preparation ID from the barcode label 113 of the container 110, by using a barcode reader 331. Reading the barcodes twice by using the barcode units 240, 330 in the sampler operation as described above can prevent mix-up of the containers 110.

When the container 110 is placed at an aspirating position 323, the specimen preparation part 33 causes a lower end of the aspiration tube 32a to penetrate the cap portion 112 of the container 110 and aspirates the sample or the blood preparation held in the container 110 through the aspiration tube 32a. The container 110 for which the aspiration is completed is transferred forward by the drive of the holder 321. Then, the agitator 310 takes out the container 110 from the holder 321 and returns the taken-out container 110 into the original holder 121 of the rack 120.

When the operations of take-out and aspiration are performed for all containers 110 held in the rack 120, the rack 120 is transported leftward and placed behind the storage portion 230. Then, the rack 120 is transported forward and stored in the storage portion 230.

Note that, in the manual operation, the operator manually turns over the container 110 in advance to agitate the liquid in the container 110. In the manual operation, the holder 321 of the container transporter 320 is transferred through a window 301 to the front thereof, the window 301 provided on a front face of the measurement unit 30 and configured to be closable and openable. Then, the operator installs the container 110 in the holder 321. Thereafter, as in the aforementioned sampler operation, the barcode unit 330 reads the barcode of the container 110 at the position 322 and the liquid in the container 110 is aspirated at the aspirating position 323. The holder 321 transports the container 110 for which the aspiration is completed forward and places the container 110 in front of the window 301. Then, the operator takes out the container 110 from the holder 321.

Figure 5:
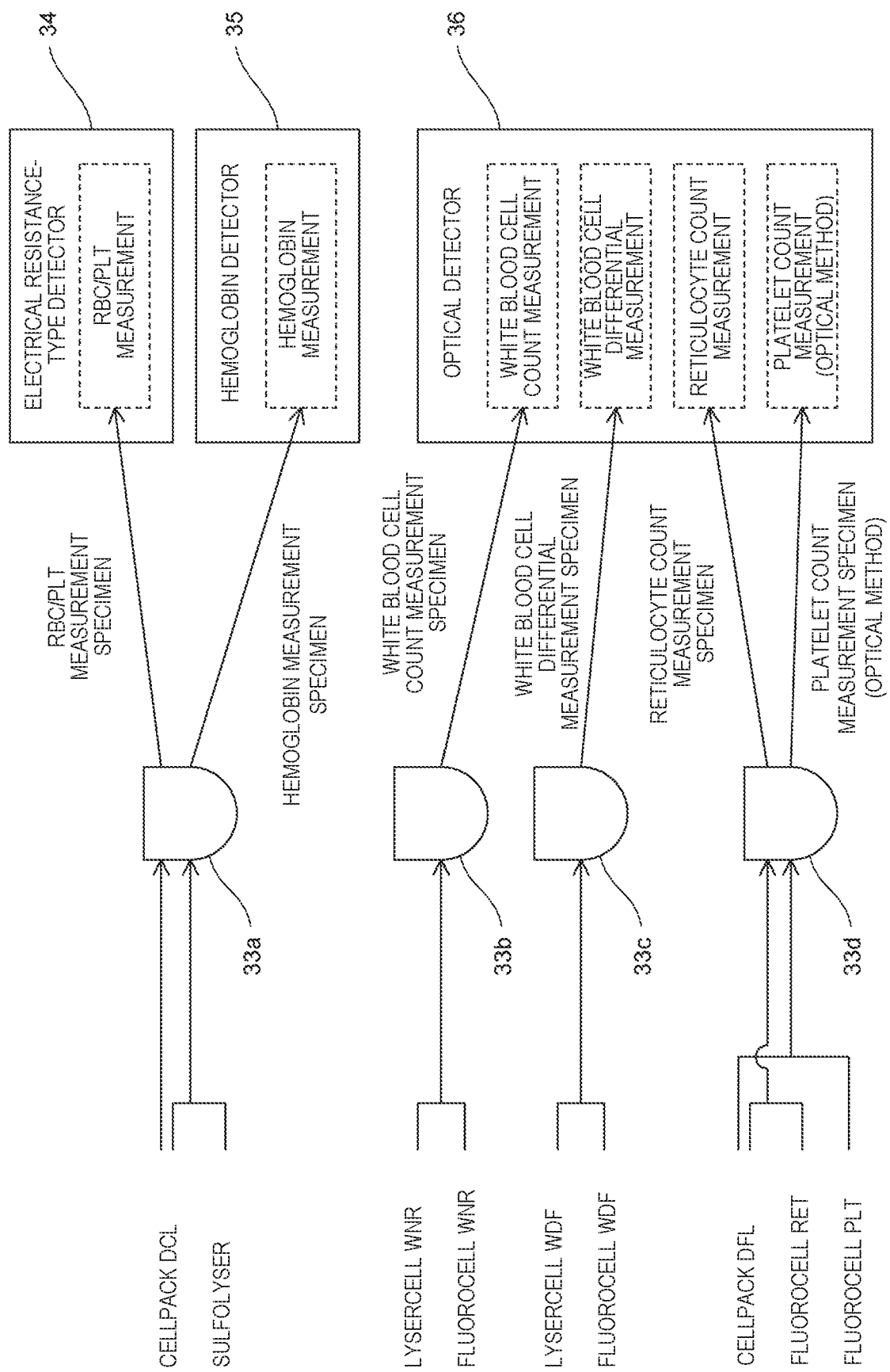
FIG. 5 is a diagram illustrating relationships among reagents, chambers, measurement specimens, and detectors according to an embodiment 1.

Next, the reagents mixed in the specimen preparation part 33, the measurement specimens prepared in the specimen preparation part 33, and the detectors that measure the measurement specimens are described with reference to FIG. 5.

The specimen preparation part 33 includes chambers 33a to 33d for mixing the samples or the blood preparations with the reagents. The samples or the blood preparations aspirated by the aspirator 32 are supplied to the chambers 33a to 33d. Moreover, various reagents are supplied to the chambers 33a to 33d.

Specifically, "Cellpack DCL" and "Sulfolyser" are supplied to the chamber 33a as the reagents. "Lysercell WNR" and "Fluorocell WNR" are supplied to the chamber 33b as the reagents. "Lysercell WDF" and "Fluorocell WDF" are supplied to the chamber 33c as the reagents. "Cellpack DFL," "Fluorocell RET," and "Fluorocell PLT" are supplied to the chamber 33d as the reagents. These reagents are all manufactured by Sysmex Corporation. Cellpack, Sulfolyser, Lysercell, Fluorocell, DCL, WNR, WDF, DFL, and RET are all registered trademarks.

In the following description, "Cellpack DCL," "Lysercell WNR," "Fluorocell WNR," "Lysercell WDF," "Fluorocell WDF," "Cellpack DFL," "Fluorocell RET," and "Fluorocell PLT" are referred to as "CellpackDCL," "LysercellWNR," "FluorocellWNR," "LysercellWDF," "FluorocellWDF," "CellpackDFL," "FluorocellRET," and "FluorocellPLT," respectively, for the sake of convenience In the chamber 33a, the sample or the blood preparation is mixed with CellpackDCL to prepare the RBC/PLT measurement specimen for measuring the red blood cells and the platelets. Moreover, in the chamber 33a, the sample or the blood preparation is mixed with the CellpackDCL and Sulfolyser to prepare the hemoglobin measurement specimen for measuring the hemoglobin concentration. In the chamber 33b, the sample is mixed with LysercellWNR and FluorocellWNR to prepare the white blood cell count measurement specimen for measuring the white blood cells and for measuring the basophil and the nucleated red blood cells.

In the chamber 33c, the sample or the blood preparation is mixed with LysercellWDF and FluorocellWDF to prepare the white blood cell differential measurement specimen for measuring neutrophils, lymphocytes, monocytes, and eosinophils and for measuring abnormal cells such as immature white blood cells and atypical lymphocytes. In the chamber 33d, the sample or the blood preparation is mixed with CellpackDFL and FluorocellRET to prepare the reticulocyte count measurement specimen for measuring reticulocytes and immature red blood cells. Moreover, in the chamber 33d, the sample or the blood preparation is mixed with CellpackDFL and FluorocellPLT to prepare the platelet count measurement specimen (optical method) for measuring the platelets.

Note that CellpackDCL is used also as a sheath liquid in the electrical resistance-type detector 34 and the optical detector 36, and is used also for cleaning of the chambers. LysercellWNR is used also for cleaning of flow paths in the measurement unit 30.

The electrical resistance-type detector 34 measures the RBC/PLT measurement specimen. The hemoglobin detector 35 measures the hemoglobin measurement specimen. The optical detector 36 separately measures the white blood cell count measurement specimen, the white blood cell differential measurement specimen, the reticulocyte count measurement specimen, and the platelet count measurement specimen (optical method). Hereafter, the measurements of the RBC/PLT measurement specimen, the hemoglobin measurement specimen, the white blood cell count measurement specimen, the white blood cell differential measurement specimen, the reticulocyte count measurement specimen, and the platelet count measurement specimen (optical method) are referred to as "RBC/PLT measurement," "hemoglobin measurement," "white blood cell count measurement," "white blood cell differential measurement," "reticulocyte count measurement," and "platelet count measurement (optical method)," respectively.

Next, the configurations of the electrical resistance-type detector 34, the hemoglobin detector 35, and the optical detector 36 are described with reference to FIGS. 6A to 6C.

As illustrated in FIG. 6A, a flow cell 34a of the electrical resistance-type detector 34 includes a specimen nozzle 411, a chamber 412, an aperture 413, and a collection tube 414.

The specimen nozzle 411 sends out the RBC/PLT measurement specimen upward together with the sheath liquid. The chamber 412 has a tapered shape which becomes narrower toward the upper side. The RBC/PLT measurement specimen passes the aperture 413 and proceeds to the collection tube 414. Blood cells included in the RBC/PLT measurement specimen flow through the aperture 413 while being aligned in single file. In the RBC/PLT measurement, a direct current is supplied between electrodes of the aperture 413, and the electrical resistance-type detector 34 detects changes in direct-current resistance which occur when the RBC/PLT measurement specimen passes the aperture 413. Since the direct-current resistance increases when the blood cells in the RBC/PLT measurement specimen pass the aperture 413, a detection signal reflects information on the blood cells passing aperture 413. The electrical resistance-type detector 34 outputs the detection signal to the signal processing circuit 37 in the later stage.

As illustrated in FIG. 6B, the hemoglobin detector 35 includes a cell 421, a light emitting diode 422, and a light receiving element 423.

The cell 421 is made of a plastic material with high translucency. The light emitting diode 422 emits light with such a wavelength that a large percentage of the light is absorbed by SLS-hemoglobin, to the cell 421. The light receiving element 423 is arranged opposite to the light emitting diode 422 with the cell 421 therebetween and receives the light transmitted through the cell 421. The hemoglobin measurement specimen is supplied to the cell 421. The light emitting diode 422 emits light with the hemoglobin measurement specimen held in the cell 421, and the light receiving element 423 receives the transmitted light. The light receiving element 423 receives only the transmitted light not absorbed by the hemoglobin measurement specimen in the light emitted from the light emitting diode 422. The light receiving element 423 detects the intensity of the transmitted light. The detection signal obtained in this case corresponds to the absorbance. The hemoglobin detector 35 outputs the detection signal to the signal processing circuit 37 in the later stage.

As illustrated in FIG. 6C, the optical detector 36 includes a flow cell 431, a light source 432, a collimator lens 433, a condenser lens 434, a beam stopper 435, a light receiving portion 436, a condenser lens 437, a dichroic mirror 438, a light receiving portion 439, an optical filter 440, and a light receiving portion 441.

The white blood cell count measurement specimen, the white blood cell differential measurement specimen, the reticulocyte count measurement specimen, and the platelet count measurement specimen (optical method) are separately supplied to the flow cell 431 together with a sheath liquid. The flow cell 431 has a tubular shape and is made of a translucent material. Particles included in the measurement specimen passes an inside of the flow cell 431 while being aligned in single file. The light source 432 is a semiconductor laser light source and emits laser light of a predetermined wavelength. The light emitted from the light source 432 excites dye included in the measurement specimen and fluorescence of a predetermined wavelength is generated from the dye.

The collimator lens 433 and the condenser lens 434 focus the light emitted from the light source 432 to cast the light on the measurement specimen flowing inside the flow cell 431. When the light from the light source 432 is casted on the measurement specimen, forward scattered light, side scattered light, and fluorescence are generated from the particles in the measurement specimen. The forward scattered light reflects information on the sizes of the particles, the side scattered light reflects information on the interiors of the particles, and the fluorescence reflects the degrees of staining of the particles. Light transmitted through the flow cell 431 without being casted on the particles in the light casted on the flow cell 431 is blocked by the beam stopper 435. The light receiving portion 436 is configured by, for example, a photodiode. The light receiving portion 436 receives the forward scattered light and outputs a detection signal corresponding to the received forward scattered light.

The condenser lens 437 focuses the side scattered light and the fluorescence generated on a lateral side of the flow cell 431. The dichroic mirror 438 reflects the side scattered light focused by the condenser lens 437 and transmits the fluorescence focused by the condenser lens 437. The light receiving portion 439 is configured by, for example, a photodiode. The light receiving portion 439 receives the side scattered light reflected by the dichroic mirror 438 and outputs a detection signal corresponding to the received side scattered light. The optical filter 440 transmits only light corresponding to a wavelength band of fluorescence to be received by the light receiving portion 441 in the light transmitted through the dichroic mirror 438. The light receiving portion 441 is configured by, for example, an avalanche photodiode. The light receiving portion 441 receives the fluorescence transmitted through the optical filter 440 and outputs a detection signal corresponding to the received fluorescence. The optical detector 36 thereby outputs the detection signals of the light receiving portions 436, 439, 441 to the signal processing circuit 37 in the later stage.

Next, the measurement modes in the blood analyzer 10 are described with reference to FIG. 7.

The blood analyzer 10 includes whole blood modes as the measurement modes for the case where the whole blood is set as the measurement target. The whole blood modes for the whole blood include a "CBC mode," a "CBC+DIFF mode," a "CBC+DIFF+RET mode," a "CBC+DIFF+RET+PLT-F mode," and the like. In the CBC mode, the RBC/PLT measurement, the hemoglobin measurement, and the white blood cell count measurement are performed. In the CBC+DIFF mode, the white blood cell differential measurement is performed in addition to the measurements in the CBC mode. In the CBC+DIFF+RET mode, the reticulocyte count measurement is performed in addition to the measurements in the CBC+DIFF mode. In the CBC+DIFF+RET+PLT-F mode, the platelet count measurement (optical method) is performed in addition to the measurements in the CBC+DIFF+RET mode.

When the controller 41 receives the whole blood as the measurement target, the controller 41 measures the RBC/PLT measurement specimen prepared based on the whole blood by using the electrical resistance-type detector 34 and obtains the red blood cell count, that is the RBC. Moreover, in this case, the controller 41 measures the white blood cell count measurement specimen prepared based on the whole blood by using the optical detector 36 and obtains the white blood cell count, that is the WBC. Furthermore, in a whole blood mode including no platelet count measurement (optical method), the controller 41 measures the RBC/PLT measurement specimen prepared based on the whole blood by using the electrical resistance-type detector 34 and obtains the platelet count, that is the PLT. In a whole blood mode including the platelet count measurement (optical method), the controller 41 measures the platelet count measurement specimen (optical method) prepared based on the whole blood by using the optical detector 36 and obtains the platelet count, that is the PLT.

The blood analyzer 10 includes blood preparation measurement modes as the measurement modes for the case where the blood preparation is set as the measurement target.

The blood preparation measurement modes for the blood preparation includes the "red blood cell preparation measurement mode," the "red blood cell preparation+remaining blood cell measurement mode," the "plasma preparation measurement mode," the "platelet preparation measurement mode," and the "platelet preparation+remaining blood cell measurement mode." In the red blood cell preparation measurement mode, the RBC/PLT measurement and the hemoglobin measurement are performed. In the red blood cell preparation+remaining blood cell measurement mode, the white blood cell differential measurement is performed in addition to the measurements in the red blood cell preparation measurement mode. In the plasma preparation measurement mode, the white blood cell differential measurement and the reticulocyte count measurement are performed. In the platelet preparation measurement mode, the RBC/PLT measurement, the hemoglobin measurement, and the platelet count measurement (optical method) are performed. In the platelet preparation+remaining blood cell measurement mode, the white blood cell differential measurement and the reticulocyte count measurement are performed in addition to the measurements in the platelet preparation measurement mode.

When the controller 41 receives the red blood cell preparation as the measurement target, that is, when the red blood cell preparation measurement mode or the red blood cell preparation+remaining blood cell measurement mode is specified, the controller 41 measures the RBC/PLT measurement specimen prepared based on the red blood cell preparation by using the electrical resistance-type detector 34, and obtains the red blood cell count, that is the RBC. Moreover, when the red blood cell preparation+remaining blood cell measurement mode is specified, the controller 41 measures the white blood cell differential measurement specimen prepared based on the red blood cell preparation by using the optical detector 36 and obtains the count of white blood cells remaining in the red blood cell preparation, that is the WBC.

When the controller 41 receives the plasma preparation as the measurement target, that is when the plasma preparation measurement mode is specified, the controller 41 measures the white blood cell differential measurement specimen prepared based on the plasma preparation by using the optical detector 36 and obtains the count of white blood cells remaining in the plasma preparation, that is the WBC. Moreover, in this case, the controller 41 measures the reticulocyte count measurement specimen prepared based on the plasma preparation by using the optical detector 36 and obtains the count of red blood cells remaining in the plasma preparation, that is the RBC.

When the controller 41 receives the platelet preparation as the measurement target, that is when the platelet preparation measurement mode or the platelet preparation+remaining blood cell measurement mode is specified, the controller 41 measures the platelet count measurement specimen (optical method) prepared based on the platelet preparation by using the optical detector 36 and obtains the platelet count, that is the PLT. Moreover, when the platelet preparation+remaining blood cell measurement mode is specified, the controller 41 measures the white blood cell differential measurement specimen prepared based on the platelet preparation by using the optical detector 36 and obtains the count of white blood cells remaining in the platelet preparation, that is the WBC. Moreover, in this case, the controller 41 measures the reticulocyte count measurement specimen prepared based on the platelet preparation by using the optical detector 36 and obtains the count of red blood cells remaining in the platelet preparation, that is the RBC.

The controller 41 can set the measurement mode to any of the whole blood modes and the blood preparation measurement modes depending on the input of the operator. Making the measurement mode switchable to any of the whole blood modes and the blood preparation measurement modes as described above eliminates the need for the operator to measure the blood preparation and the whole blood separately by using devices.

Note that the measurement targets of the blood analyzer 10 may include only the blood preparations. Specifically, the blood analyzer 10 may only have the blood preparation measurement mode. In this case, the blood analyzer 10 is a device that measures and analyzes only the blood preparations and the measurement mode is always the blood preparation measurement mode.

FIG. 8 is a flowchart illustrating processing of receiving the input of the measurement mode and preparing the measurement specimen depending on the received measurement mode.

In step S11, the controller 41 receives the blood preparation measurement mode or the whole blood mode through a screen 500 to be described later with reference to FIG. 9A. Specifically, in step S11, the controller 41 receives one of the blood preparation and the whole blood as the measurement target. In step S12, the controller 41 determines whether the measurement mode received in step S11 is the blood preparation measurement mode. When the received measurement mode is the blood preparation measurement mode, the controller 41 causes the processing to proceed to step S13. When the received measurement mode is the whole blood mode, the controller 41 causes the processing proceed to step S15.

In step S13, the controller 41 receives one of the blood preparation measurement modes selected from the red blood cell preparation measurement mode, the red blood cell preparation+remaining blood cell measurement mode, the plasma preparation measurement mode, the platelet preparation measurement mode, and the platelet preparation+ remaining blood cell measurement mode illustrated in FIG. 7, through the reception screen 600 to be described later with reference to FIG. 9B. In step S14, the controller 41 prepares the measurement specimen based on the blood preparation aspirated by the aspirator 32, depending on the blood preparation measurement mode received in step S13. The measurement specimen is prepared depending on the type of measurement to be performed in the received blood preparation measurement mode. Thereafter, the controller 41 performs the measurement and the analysis as described with reference to FIG. 10 by using the measurement specimen prepared in step S14.

In step S15, the controller 41 receives one of the whole blood modes selected from the CBC mode, the CBC+DIFF mode, the CBC+DIFF+RET mode, and the CBC+DIFF+ RET+PLT-F mode illustrated in FIG. 7. In step S16, the controller 41 prepares the measurement specimen based on the whole blood aspirated by the aspirator 32, depending on the whole blood mode received in step S15. The measurement specimen is prepared based on the type of measurement to be performed in the received whole blood mode. Thereafter, the controller 41 performs the measurement and the analysis by using the measurement specimen prepared in step S16.

FIG. 9A is a diagram illustrating the screen 500 for changing the measurement target. The screen 500 is displayed on the display part 43 by the operator operating a menu or the like displayed on the display part 43.

As illustrated in FIG. 9A, the screen 500 for changing the measurement target includes a button 511 for specifying the whole blood, a button 512 for specifying the blood preparation, an OK button 521, and a cancel button 522. The operator can operate the buttons 511, 512 to change selection states of the operated buttons. The operator can select one of the buttons 511, 512.

When the operator operates the OK button 521 with the button 511 being selected, the controller 41 closes the screen 500 and displays a screen for setting the measurement mode to one of the whole blood modes illustrated in FIG. 7, on the display part 43. When the controller 41 receives an input of whole blood mode through this screen, the controller 41 controls the specimen preparation part 33 such that the specimen preparation part 33 mixes the whole blood in the container 110 with the reagent to prepare the measurement specimen, and controls the measurement part 30a such that the measurement part 30a measures the prepared measurement specimen.

Meanwhile, when the operator operates the OK button 521 with the button 512 being selected, the controller 41 closes the screen 500 and displays the reception screen 600 for setting the measurement mode to one of the blood preparation measurement modes illustrated in FIG. 7, on the display part 43. When the controller 41 receives an input of one blood preparation measurement mode through the reception screen 600, the controller 41 controls the specimen preparation part 33 such that the specimen preparation part 33 mixes the blood preparation in the container 110 with the reagent to prepare the measurement specimen, and controls the measurement part 30a such that the measurement part 30a measures the prepared measurement specimen.

When the operator operates the cancel button 522, the controller 41 cancels the selection state of the button on the screen 500 and closes the screen 500.

FIG. 9B is a diagram illustrating the reception screen 600 for setting one of the blood preparation measurement modes by receiving the input of the one blood preparation measurement mode.

The reception screen 600 includes a button 610 for specifying the red blood cell preparation, a button 611 for specifying the measurement of the white blood cells remaining in the red blood cell preparation, a button 620 for specifying the plasma preparation, a button 630 for specifying the platelet preparation, a button 631 for specifying the measurement of the red blood cells and the white blood cells remaining in the platelet preparation, an OK button 641, and a cancel button 642.

The operator can operate the buttons 610, 611, 620, 630, 631 to change selection states of the operated buttons. The operator can select one of the buttons 610, 620, 630. The button 611 is set to a selectable state when the button 610 is selected. The button 631 is set to a selectable state when the button 630 is selected. In the state illustrated in FIG. 9B, since neither of the buttons 610, 630 are selected, the buttons 611, 631 are set to an unselectable state.

When the operator operates the OK button 641 with only the button 610 being selected, the controller 41 sets the measurement mode to the red blood cell preparation measurement mode. When the operator operates the OK button 641 with the buttons 610, 611 being selected, the controller 41 sets the measurement mode to the red blood cell preparation+remaining blood cell measurement mode. When the operator operates the OK button 641 with the button 620 being selected, the controller 41 sets the measurement mode to the plasma preparation measurement mode. When the operator operates the OK button 641 with only the button 630 being selected, the controller 41 sets the measurement mode to the platelet preparation measurement mode. When the operator operates the OK button 641 with the buttons 630, 631 being selected, the controller 41 sets the measurement mode to the platelet preparation+remaining blood cell measurement mode. The controller 41 stores the set blood preparation measurement mode in the memory 42.

When the operator operates the cancel button 642, the controller 41 cancels the selection state of the button on the reception screen 600 and closes the reception screen 600.

Providing the buttons 610, 611, 630, 631 for selecting the blood preparation measurement modes as described above allows the operator to select a way of use matching an utilization mode of the blood analyzer 10, for example, select the buttons 610, 630 in a step of testing the components of the blood preparation and select the buttons 611, 631 in a step of testing the blood cells remaining in the blood preparation.

Configuring the reception screen 600 as described above allows the operator to set the measurement mode to the red blood cell preparation measurement mode by selecting the button 610 and measure the red blood cells in the red blood cell preparation. The operator can set the measurement mode to the red blood cell preparation+remaining blood cell measurement mode by selecting the buttons 610, 611, and measure the red blood cells in the red blood cell preparation and the white blood cells remaining in the red blood cell preparation. The operator can set the measurement mode to the plasma preparation measurement mode by selecting the button 620 and measure the red blood cells and the white blood cells remaining in the plasma preparation. The operator can set the measurement mode to the platelet preparation measurement mode by selecting the button 630 and measure the platelets in the platelet preparation. The operator can select the platelet preparation+remaining blood cell measurement mode by selecting the buttons 630, 631 and measure the platelets in the platelet preparation and the red blood cells and the white blood cells remaining in the platelet preparation. As described above, the operator can measure the blood cells being main components in the blood preparations and measure the blood cells which are to be removed but remain in the blood preparations, only by operating the buttons to input the blood preparation measurement modes.

Note that, in the plasma preparation measurement mode and the platelet preparation+remaining blood cell measurement mode, there is no need to measure both of the remaining red blood cells and the remaining white blood cells and only one of these may be measured. Moreover, the reception screen 600 in FIG. 9B may be configured such that the button 611 is omitted and a button for selecting the red blood cell preparation+remaining blood cell measurement mode is arranged. The reception screen 600 may be configured such that the button 631 is omitted and a button for selecting the platelet preparation+remaining blood cell measurement mode is arranged. Moreover, when a mode for measuring only the blood cells remaining in the red blood cell preparation and a mode for measuring only the blood cells remaining in the platelet preparation are provided as the blood preparation measurement modes, buttons corresponding to these modes may be arranged in the reception screen 600.

The controller 41 may receive the inputs of the blood preparation measurement modes, by using, instead of the reception screen 600, a physical button mechanism corresponding to the blood preparation measurement modes. Moreover, when the blood preparation ID read from the barcode of the container 110 includes the blood preparation measurement mode, the controller 41 may receive the input of the blood preparation measurement mode based on the read blood preparation ID.

In the sampler operation, the operator sets the measurement mode to one of the blood preparation measurement modes in the reception screen 600, then causes the rack 120 to hold the containers 110 holding the type of blood preparation corresponding to the set blood preparation measurement mode, and installs the rack 120 in the storage portion 210. As described with reference to FIG. 3, the blood analyzer 10 thus automatically transports the rack 120, supplies the containers 110 held in the rack 120 to the measurement unit 30 one by one, and measures the blood preparation in each container 110. Meanwhile, in the manual operation, the operator sets the measurement mode to one of the blood preparation measurement modes in the reception screen 600 and then installs the container 110 which holds the type of blood preparation corresponding to the set blood preparation measurement mode and for which the agitation operation has been already performed, in the holder 321 of the container transporter 320. As described with reference to FIG. 3, the blood analyzer thus supplies the container 110 to the measurement unit 30 and measures the blood preparation in the container 110.

When the whole blood mode is set, the rack 120 or the operator supplies the container 110 holding the whole blood to the measurement unit 30 and the measurement unit 30 measures the whole blood in the container 110 in a similar way.

Next, control performed by the controller 41 depending on the blood preparation measurement mode set through the reception screen 600 is described with reference to the flowchart in FIG. 10.

Figure 10:
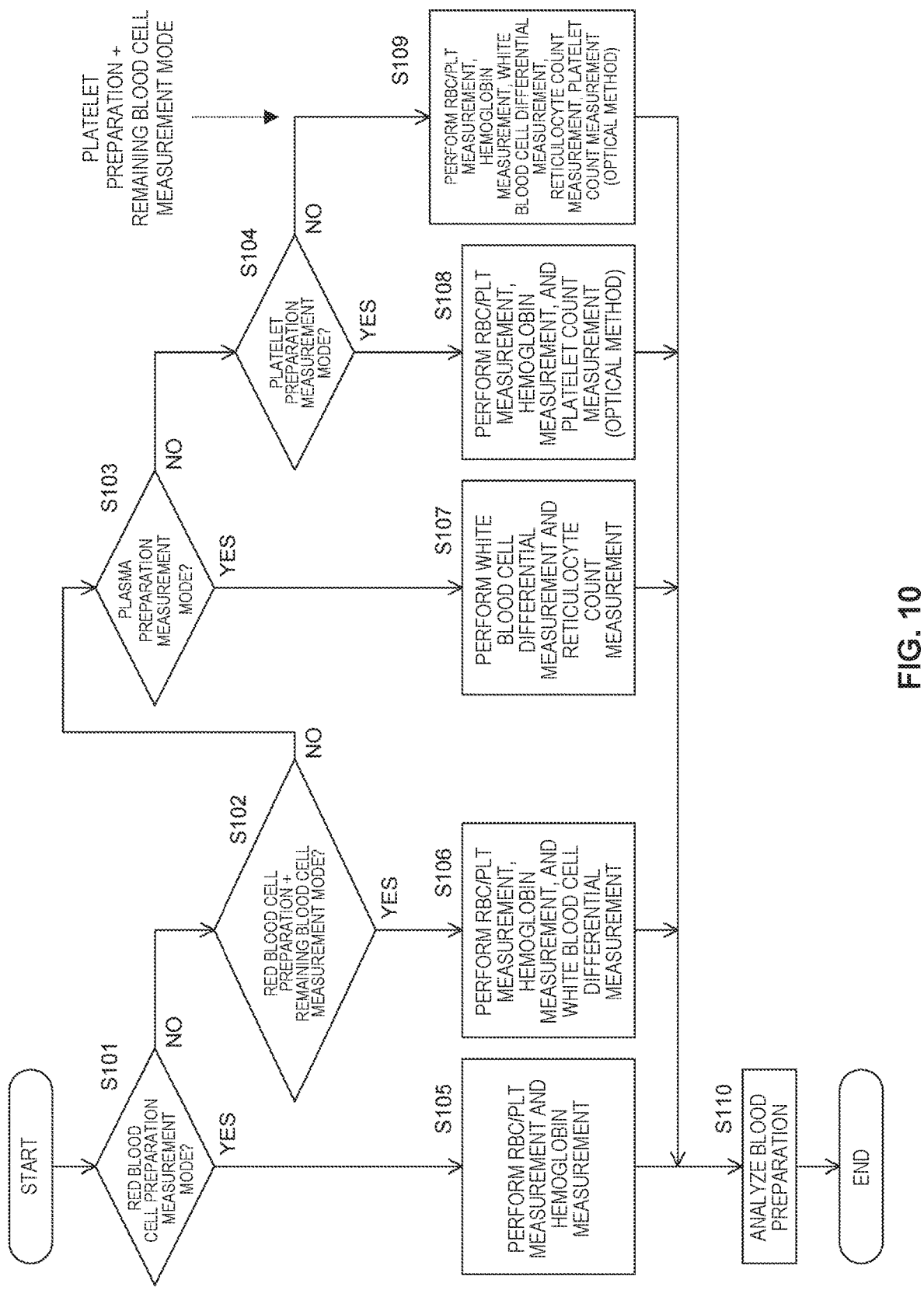
FIG. 10 is a flowchart illustrating control performed by a controller depending on a blood preparation measurement mode according to an embodiment 1.

The processing in FIG. 10 starts when the operator performs the setting through the reception screen 600 in FIG. 9B and then the blood analyzer 10 supplies the container 110 to the measurement unit 30 and aspirates the blood preparation from the container 110 by using the aspirator 32 to prepare the measurement specimen in step S14 in FIG. 8.

In steps S101 to S104, the controller 41 reads the blood preparation measurement mode set through the reception screen 600 in FIG. 9B from the memory 42 and causes the processing to proceed to one of steps S105 to S109 depending on the read blood preparation measurement mode. Specifically, the controller 41 causes the processing to proceed to step S105 when the read blood preparation measurement mode is the red blood cell preparation measurement mode, to step S106 when it is the red blood cell preparation+remaining blood cell measurement mode, to step S107 when it is the plasma preparation measurement mode, to step S108 when it is the platelet preparation measurement mode, and to step S109 when it is the platelet preparation+remaining blood cell measurement mode.

When the blood preparation measurement mode is the red blood cell preparation measurement mode, in step S105, the controller 41 performs the RBC/PLT measurement based on the RBC/PLT measurement specimen and the hemoglobin measurement based on the hemoglobin measurement specimen. When the blood preparation measurement mode is the red blood cell preparation+remaining blood cell measurement mode, in step S106, the controller 41 performs the RBC/PLT measurement based on the RBC/PLT measurement specimen, the hemoglobin measurement based on the hemoglobin measurement specimen, and the white blood cell differential measurement based on the white blood cell differential measurement specimen.

When the blood preparation measurement mode is the plasma preparation measurement mode, in step S107, the controller 41 performs the white blood cell differential measurement based on the white blood cell differential measurement specimen and the reticulocyte count measurement based on the reticulocyte count measurement specimen.

When the blood preparation measurement mode is the platelet preparation measurement mode, in step S108, the controller 41 performs the RBC/PLT measurement based on the RBC/PLT measurement specimen, the hemoglobin measurement based on the hemoglobin measurement specimen, and the platelet count measurement (optical method) based on the platelet count measurement specimen (optical method). When the blood preparation measurement mode is the platelet preparation+remaining blood cell measurement mode, in step S109, the controller 41 performs the RBC/PLT measurement based on the RBC/PLT measurement specimen, the hemoglobin measurement based on the hemoglobin measurement specimen, the white blood cell differential measurement based on the white blood cell differential measurement specimen, the reticulocyte count measurement based on the reticulocyte count measurement specimen, and the platelet count measurement (optical method) based on the platelet count measurement specimen (optical method).

The controller 41 obtains the measurement data on the blood preparation set as the measurement target by performing the processing in one of steps S105 to S109. The contents of the measurement processing performed by the controller 41 in step S105 to S109 are described later with reference to FIG. 11.

When the measurement of the blood preparation is completed, in step S110, the controller 41 analyzes the blood preparation by using the measurement data based on the blood preparation. In the analysis of step S110, the controller 41 obtains the resultant value of each of measurement items as the measurement result. The measurement items to be obtained vary depending on the blood preparation measurement mode. The measurement items to be obtained are described later with reference to FIGS. 12A to 14B.

FIG. 11 is a table describing in detail processing setting for each of steps S105 to S109 in FIG. 10, that is processing setting depending on the blood preparation measurement mode.

The first row in FIG. 11 describes the measurements in the red blood cell preparation measurement mode in step S105. The second row in FIG. 11 describes the measurements in the red blood cell preparation+remaining blood cell measurement mode in step S106. The third row in FIG. 11 describes the measurements in the plasma preparation measurement mode in step S107. The fourth row in FIG. 11 describes the measurements in the platelet preparation measurement mode in step S108. The fifth row in FIG. 11 describes the measurements in the platelet preparation+remaining blood cell measurement mode in step S109. Moreover, the items of the measurement channels describe the types of measurements performed in the blood preparation measurement modes of the respective rows as illustrated in steps S105 to S109 in FIG. 10.

Here, the measurements of each blood preparation are not necessarily performed in the same way as the measurements of the whole blood and, as illustrated in FIG. 11, are performed partially differently from the measurements of the whole blood.

Specifically, in the red blood cell preparation measurement mode, the RBC/PLT measurement and the hemoglobin measurement are performed substantially in the same setting as that for the whole blood. In detail, the volume of the red blood cell preparation used in the RBC/PLT measurement and the hemoglobin measurement are substantially the same as the volume of the whole blood used in these measurements. As described above, "same setting as whole blood" means that the setting relating to the measurement such as the volumes of the blood preparation and the reagent used in the measurement is substantially the same as that for the whole blood. Note that the container 110 is agitated in the sampler operation as described with reference FIG. 4B. In the red blood cell preparation+remaining blood cell measurement mode, the RBC/PLT measurement and the hemoglobin measurement are performed in the same way as for the whole blood, but the white blood cell differential measurement is performed in high-sensitivity setting. The high-sensitivity setting is described later.

In the plasma preparation measurement mode, the white blood cell differential measurement and the reticulocyte count measurement are performed in the high-sensitivity setting. In the platelet preparation measurement mode, the RBC/PLT measurement and the hemoglobin measurement are performed in the high-sensitivity setting but the platelet count measurement (optical method) is performed substantially in the same setting as for the whole blood. In the platelet preparation+remaining blood cell measurement mode, the RBC/PLT measurement, the hemoglobin measurement, the white blood cell differential measurement, and the reticulocyte count measurement are performed in the high-sensitivity setting, and the platelet count measurement (optical method) is performed substantially in the same setting as for the whole blood.

Here, when the blood preparations are measured in the high-sensitivity setting, the blood cells can be measured with higher sensitivity than that in the case where the whole blood is measured in normal setting. Specifically, in the white blood cell differential measurement, the amount of blood preparation used in the high-sensitivity setting is greater than the amount of whole blood used in the measurement of the whole blood in the normal setting, and the amount of white blood cell differential measurement specimen based on the blood preparation and measured in the high-sensitivity setting is greater than the amount of white blood cell differential measurement specimen based on the whole blood and measured in the normal setting. In the reticulocyte count measurement, the amount of blood preparation used in the high-sensitivity setting is greater than the amount of whole blood used in the measurement of the whole blood in the normal setting, and the amount of reticulocyte count measurement specimen based on the blood preparation and measured in the high-sensitivity setting is greater than the amount of reticulocyte count measurement specimen based on the whole blood and measured in the normal setting. Moreover, when the white blood cell differential measurement and the reticulocyte count measurement are performed based on the blood preparation in the high-sensitivity setting, the flow rate of the measurement specimen flowing through the flow cell 431 is set higher and the time in which the measurement specimen is made to flow through the flow cell 431 are set longer than those in the case where the white blood cell differential measurement and the reticulocyte count measurement are performed based on the whole blood in the normal setting.

Moreover, in the RBC/PLT measurement, the amount of RBC/PLT measurement specimen based on the blood preparation and measured in the high-sensitivity setting is greater than the amount of RBC/PLT measurement specimen based on the whole blood and measured in the normal setting. Moreover, when the RBC/PLT measurement is performed based on the blood preparation in the high-sensitivity setting, the time in which the measurement specimen is made to flow through the flow cell 431 is set longer than that in the case where the RBC/PLT measurement is performed based on the whole blood in the normal setting. Also in the hemoglobin measurement, the amount of measurement specimen measured and the time in which the measurement specimen is made to flow are increased in the high-sensitivity setting. In the high-sensitivity setting, the blood cells can be measured with higher sensitivity than that in the case where the whole blood is measured in the normal setting.

As described above, the controller 41 controls the measurement condition in the measurement part 30a depending on the blood preparation measurement mode. Controlling the measurement condition depending on the blood preparation measurement mode enables measurement depending on the characteristics and the like of the blood preparation.

FIGS. 12A to 14B are tables describing measurement items obtained in five blood preparation measurement modes and reagents used in the five blood preparation measurement modes. FIGS. 12A to 14B correspond to the red blood cell preparation measurement mode, the red blood cell preparation+remaining blood cell measurement mode, the plasma preparation measurement mode, the platelet preparation measurement mode, and the platelet preparation+remaining blood cell measurement mode, respectively.

In each of FIGS. 12A to 14B, an upper table describes measurement items obtained in the measurements performed in the corresponding blood preparation measurement mode and measurement channels in which the measurement items are obtained. "RBC," "PLT," and "WBC" in the measurement items are the red blood cell count, the platelet count, and the white blood cell count per unit area, respectively. Moreover, "HGB" and "HCT" in the measurement items are a hemoglobin content and a hematocrit, respectively. Furthermore, the measurement items in the upper table are measurement items with clinical significance. Note that, in the blood preparation measurement modes, resultant values of measurement items other than the measurement items illustrated in FIGS. 12A to 14B may be obtained.

As illustrated in FIGS. 12A and 12B, for the red blood cell preparation, the measurement result based on the RBC/PLT measurement is used as the resultant value of the measurement item "RBC." As illustrated in FIGS. 13 and 14B, for the plasma preparation and the platelet preparation, the measurement result based on the reticulocyte count measurement is used as the resultant value of the measurement item "RBC." As described above, the red blood cells in the red blood cell preparation and the red blood cells remaining in the blood preparations other than the red blood cell preparation are measured based on the different measurements, and this enables appropriate measurement of the red blood cells in each blood preparation.

As illustrated in FIGS. 13 and 14B, for the plasma preparation and the platelet preparation, instead of the measurement result based on the RBC/PLT measurement, the measurement result based on the reticulocyte count measurement is used as the resultant value of the measurement item "RBC." Very few red blood cells remain in these blood preparations, and the accuracy of the resultant value of the measurement item "RBC" can be thus improved by using the resultant value based on the reticulocyte count measurement, instead of the RBC/PLT measurement. Specifically, the red blood cell count is detected by performing the reticulocyte count measurement for the plasma preparation and the platelet preparation and by performing the RBC/PLT measurement for the red blood cell preparation, and the sensitivity of detecting the red blood cell count for the plasma preparation and the platelet preparation can be thereby made higher than the sensitivity of detecting the red blood cell count for the red blood cell preparation. The count of red blood cells remaining in the plasma preparation and the platelet preparation can be thereby accurately obtained.

The white blood cells and the red blood cells remaining in the blood preparation are obtained by performing the white blood cell differential measurement and the reticulocyte count measurement in setting with higher sensitivity than that in the case where the whole blood is measured in the normal setting. The few white blood cells and the few red blood cells remaining in the plasma preparation and the platelet preparation can be thereby measured with high accuracy.

In each of FIGS. 12A to 14B, a lower table describes the types of reagents used to prepare the measurement specimen in the case where the measurements described in the upper table are performed.

As illustrated in FIGS. 11 to 14B, the controller 41 controls the types and number of measurement specimens to be prepared and the types and number of reagents to be used in each measurement, depending on the blood preparation measurement mode. For example, in the processing in the red blood cell preparation measurement mode, the controller 41 prepares two types of measurement specimens, the RBC/PLT measurement specimen and the hemoglobin measurement specimen, and uses two types of reagents, CellpackDCL and Sulfolyser. Preparing the measurement specimens and using the reagents depending on the blood preparation measurement mode as described above can more surely reduce the consumption amounts of the reagents.

Figures 15A, 15B:
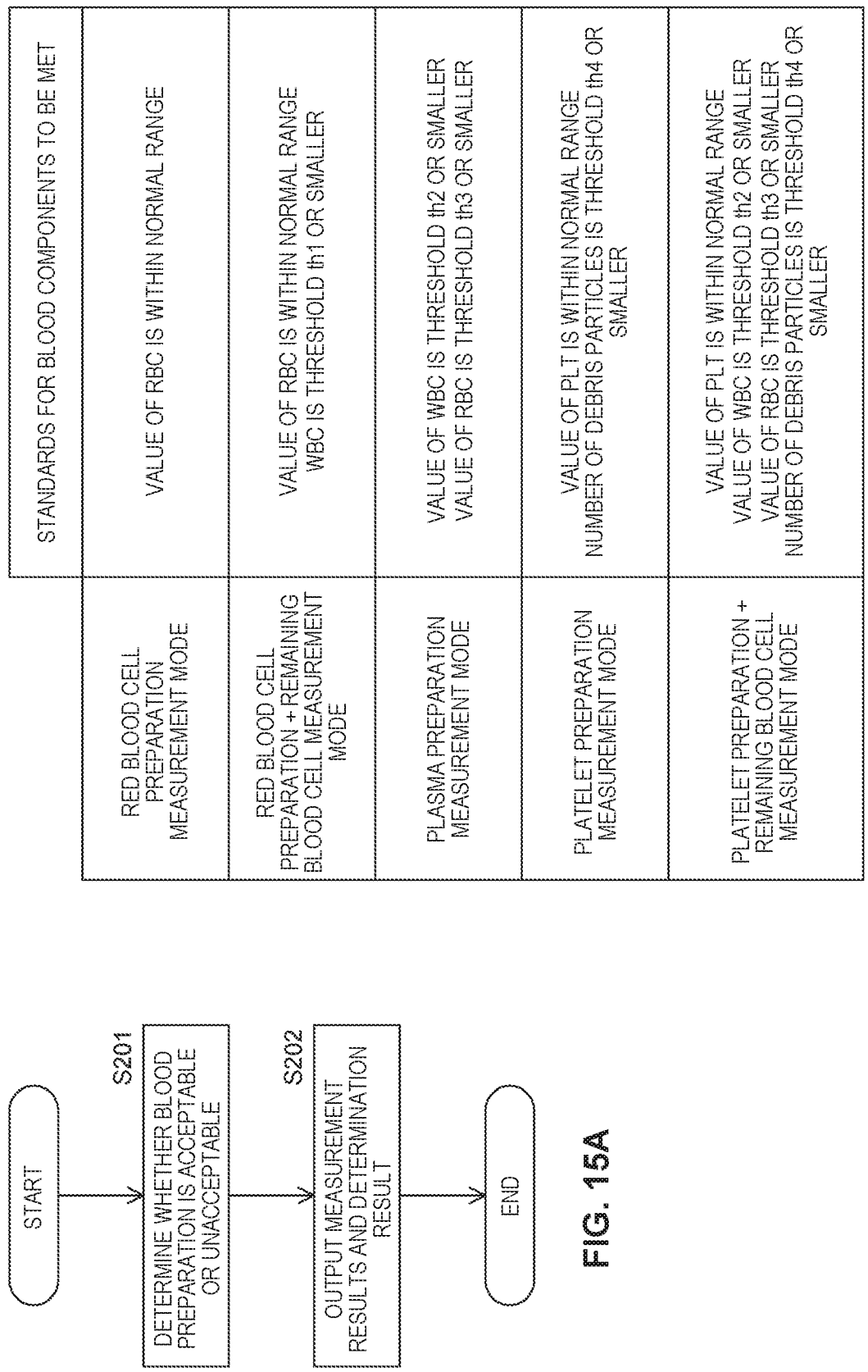
FIG. 15A is a flowchart illustrating processing of determining whether a blood preparation is acceptable or not and processing of outputting results according to an embodiment 1.
FIG. 15B is a table illustrating determination standards used in determination of whether a blood preparation is acceptable or not.

Next, processing of determining whether the blood preparation is acceptable or not and processing of outputting a result which are performed by the controller 41 are described with reference to the flowchart in FIG. 15A The processing in FIG. 15A is started when the processing in FIG. 10 is completed. In step S201, the controller 41 determines whether the blood preparation is acceptable or not based on the resultant values, that is the measurement results of the measurement items obtained in step S110 in FIG. 10 and determination standards described in FIG. 15B.

FIG. 15B is a table describing the standards for the blood components to be met by the blood preparation. First to fifth rows each describe a determination standard applied to the measurement result in the corresponding blood preparation measurement mode. As described in the first row, in the red blood cell preparation measurement mode, the quality of the red blood cell preparation is determined to be "OK" when the value of the measurement item "RBC" is within a normal range. As described in the second row, in the red blood cell preparation+remaining blood cell measurement mode, the quality of the red blood cell preparation is determined to be "OK" when the value of the measurement item "RBC" is within a normal range and the value of the measurement item "WBC" is a threshold th1 or smaller. The threshold th1 is set to, for example, three cells/μL.

As described in the third row, in the plasma preparation measurement mode, the quality of the plasma preparation is determined to be "OK" when the value of the measurement item "WBC" is a threshold th2 or smaller and the value of the measurement item "RBC" is a threshold th3 or smaller. The thresholds th2, th3 are set to, for example, four cells/μL and $1.2 \times 10^4$ cells/μL, respectively.

As described in the fourth row, in the platelet preparation measurement mode, the quality of the platelet preparation is determined to be "OK" when the value of the measurement item "PLT" is within a normal range and the number of debris particles per unit volume is a threshold th4 or smaller. As described in the fifth row, in the platelet preparation+remaining blood cell measurement mode, the quality of the platelet preparation is determined to be "OK" when: the value of the measurement item "PLT" is within the normal range; the value of the measurement item "WBC" is the threshold th2 or smaller; the value of the measurement item "RBC" is the threshold th3 or smaller; and the number of debris particles per unit volume is the threshold th4 or smaller. When the determination standard described above is not satisfied in each of the cases of the first to fifth rows, the quality of the blood preparation is determined to be "not OK."

Note that the ranges of the values of the measurement items "RBC" and "PLT" in which the values are determined to be normal and the values of the thresholds th1, th2, th3, th4 can be changed in or via a menu or the like displayed on the display part 43. This enables setting of determination standards depending on a refining step of the blood preparation, setting of determination standards depending on a quality standard determined by a country or a region, and the like. Accordingly, the quality of the blood preparation can be appropriately determined.

Moreover, although the controller 41 determines whether all of the conditions are met in each of the blood preparation measurement modes described in the second to fifth row in FIG. 15B, the controller 41 may determine whether at least one of the conditions is met when determining whether the blood preparation is acceptable or not in each blood preparation measurement mode.

Figure 16B:
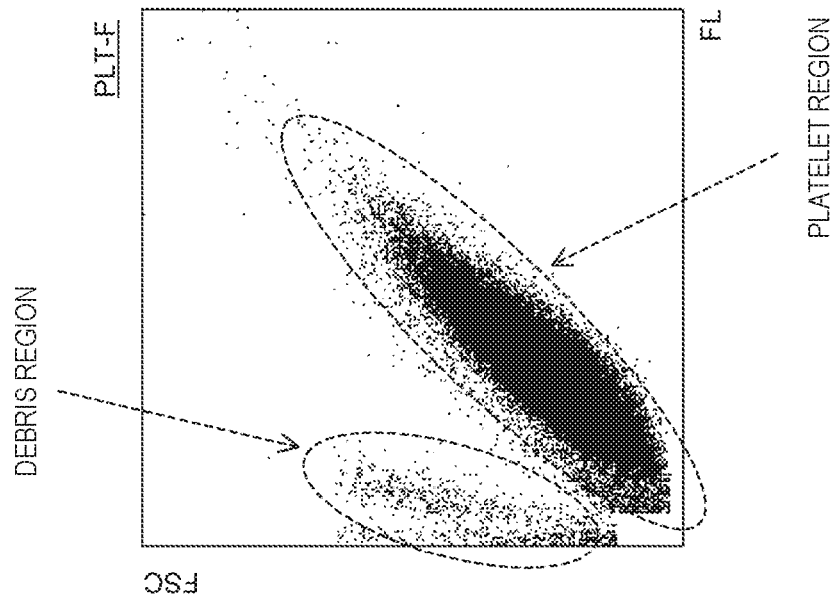
FIGS. 16A and 16B are diagrams illustrating PLT-F scattergrams referred to in determination of whether a blood preparation is acceptable or not according to an embodiment 1.
Figure 16A:
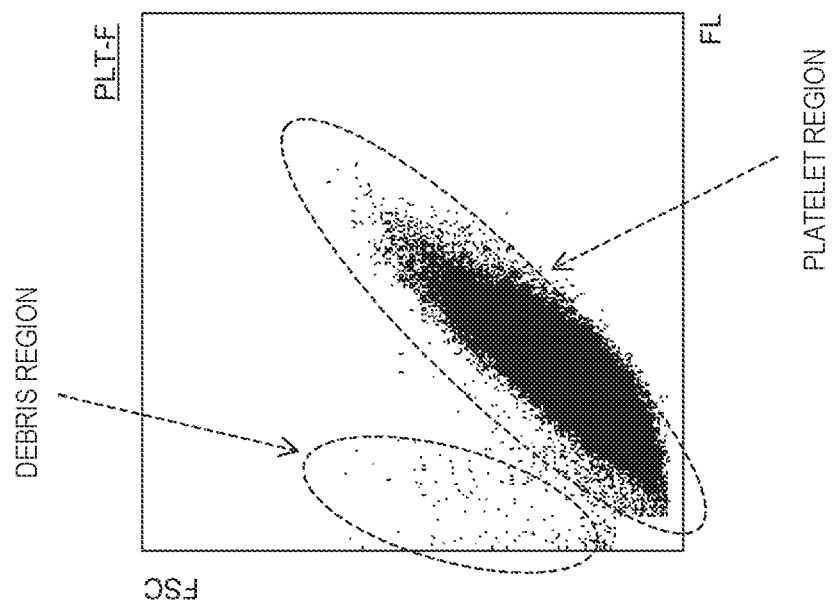

FIGS. 16A and 16B are PLT-F scattergrams referred to in the determination standards of the platelet preparation measurement mode and the platelet preparation+remaining blood cell measurement mode. In each PLT-F scattergram, the horizontal axis and the vertical axis represent, respectively, a fluorescence intensity and a forward scattered light intensity obtained based on the platelet count measurement (optical method). The fluorescence intensity is a value corresponding to the degree of staining of particles in the platelet preparation, and the forward scattered light intensity is a value corresponding to the size of particles in the platelet preparation. In each PLT-F scattergram, dots of the respective particles are plotted based on the fluorescence intensity and the forward scattered light intensity obtained for each particle. In each PLT-F scattergram, there are illustrated a platelet region in which particles corresponding to the platelets are distributed and a debris region in which particles corresponding to debris formed by degrading of the platelet preparation are distributed. The debris region is a region in which particles with a lower fluorescence intensity than the fluorescence intensity of the platelets are distributed.

FIG. 16A is a PLT-F scattergram obtained based on a measurement of a normal platelet preparation, and FIG. 16B is a PLT-F scattergram obtained based on a measurement of a degraded platelet preparation. As apparent from comparison of FIGS. 16A and 16B, the number of particles in the debris region increase as the platelet preparation degrades. From this fact, it is conceivable that the particles in the debris region, that is the particles with lower fluorescence intensity than the fluorescence intensity of the platelets correspond to degraded platelets. Accordingly, if the number of debris particles is greater than the predetermined threshold th4 as described in the determination standard in the fourth and fifth rows in FIG. 15B, it is conceivable that the quality of the platelet preparation has decreased. Hence, the controller 41 can determine the quality of the platelet preparation by obtaining the number of debris particles as the measurement result and comparing the obtained number of debris particles, that is a degraded platelet count with the determination standard.

Note that, when obtaining the number of debris particles, the controller 41 does not have to actually generate the PLT-F scattergram and count the number of particles in the debris region and, instead, obtains the number of debris particles by performing data processing equivalent to the generation of the PLT-F scattergram.

Returning to FIG. 15A, in step S202, when the controller 41 receives a display instruction from the operator, the controller 41 outputs the measurement results and the determination result on the display part 43 as illustrated in FIGS. 17 to 20. The processing in FIG. 15A is thereby completed.

Figure 17:
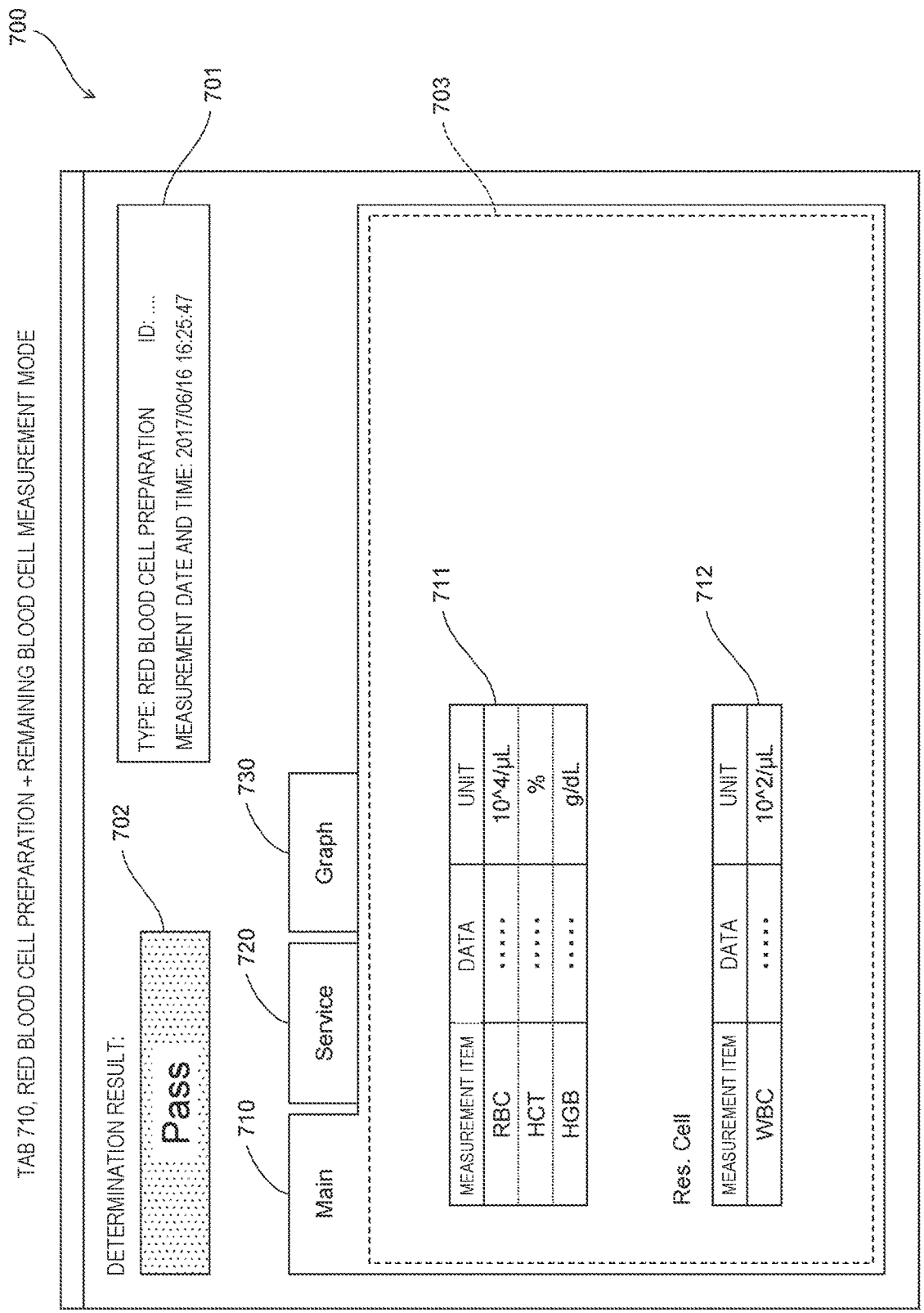
FIG. 17 is a diagram illustrating a screen for displaying a list of measurement results and a determination result for measurement results according to an embodiment 1.

FIG. 17 is a diagram illustrating a screen 700 displayed on the display part 43.

The screen 700 includes regions 701, 702, 703 and tabs 710, 720, 730. The controller 41 displays the type of blood preparation, the blood preparation ID, and the time and date of the measurement of the blood preparation in the region 701. The controller 41 displays the result of determination on whether the blood preparation is acceptable or not performed in step S201 in FIG. 15A in the region 702. In other words, the information indicating whether the quality of the blood preparation is guaranteed or not is displayed in the region 702. In response to the operation of any of the tabs 710, 720, 730, the controller 41 displays the measurement results, graphs, or the like corresponding to the operated tab in the region 703.

Figures 18A, 18B, 18C, 18D:
FIG. 18A is a diagram illustrating a region displaying a determination result in the case where there is a problem in acceptability of a blood preparation according to an embodiment 1.
FIGS. 18B and 18C are tables illustrating lists of measurement results for measurement results according to an embodiment 1.
FIG. 18D is a table illustrating a list of measurement results relating to degraded platelets according to an embodiment 1.

The example illustrated in FIG. 17 illustrates the measurement results and the like in the red blood cell preparation+remaining blood cell measurement mode. In the region 701, it is indicated that the contents of the currently-displayed screen 700 is based on the red blood cell preparation. In the region 702, "Pass" indicating that the quality of the blood preparation is "OK" is displayed. When the quality is "OK," the color inside the region 702 may be set to green so that a viewer can easily visually grasp that the blood preparation is normal. Meanwhile, when the quality of the blood preparation is "not OK," "Fail" is displayed in the region 702 as illustrated in FIG. 18A. In this case, the color inside the region 702 may be set to red so that the viewer can easily visually grasp that the blood preparation is abnormal.

Displaying the result of determination on whether the corresponding blood preparation is acceptable or not in the region 702 as described above allows the operator to smoothly and accurately grasp the quality of the blood preparation.

When the tab 710 is operated, a list 711 indicating the resultant values of the measurement items except for the measurement items of the remaining blood cells and a list 712 indicating the measurement items of the remaining blood cells are displayed in the region 703. As illustrated in FIG. 17, when the tab 710 is operated for the measurement results in the red blood cell preparation+remaining blood cell measurement mode, the list 711 indicating the resultant values of the measurement items "RBC," "HCT," and "HGB" and the list 712 indicating the resultant value of the measurement item "WBC" are displayed in the region 703 according to the upper table in FIG. 12B. Note that, in the red blood cell preparation measurement mode, the display of the list 712 is omitted.

As illustrated in FIG. 18B, when the tab 710 is operated for the measurement results in the plasma preparation measurement mode, the list 712 indicating the resultant values of the measurement items "RBC" and "WBC" are displayed in the region 703 according to the upper table in FIG. 13. In this case, the display of the list 711 is omitted.

As illustrated in FIG. 18C, when the tab 710 is operated for the measurement results in the platelet preparation+remaining blood cell measurement mode, the list 711 indicating the resultant value of the measurement item "PLT" and the list 712 indicating the resultant values of the measurement items "RBC" and "WBC" are displayed in the region 703 according to the upper table in FIG. 14B. Note that, in the platelet preparation measurement mode, the display of the list 712 is omitted.

When the tab 720 is operated, a list 721 indicating the resultant values of the other measurement results are displayed in the region 703. As illustrated in FIG. 18D, when the tab 720 is operated for the measurement results in the platelet preparation measurement mode and the platelet preparation+remaining blood cell measurement mode, the list 721 indicating the number of particles in the debris region that is the number of degraded platelets is displayed in the region 703.

As described above, the measurement result for the red blood cells in the red blood cell preparation is displayed in the red blood cell preparation measurement mode, and the measurement results for the red blood cells in the red blood cell preparation and the white blood cells remaining in the red blood cell preparation are displayed in the red blood cell preparation+remaining blood cell measurement mode. The operator can thereby check the quality of the red blood cell preparation. Moreover, the measurement results for the red blood cells and the white blood cells remaining in the plasma preparation are displayed in the plasma preparation measurement mode. The operator can thereby check the quality of the plasma preparation. Furthermore, the measurement results for the platelets and the degraded platelets in the platelet preparation are displayed in the platelet preparation measurement mode, and the measurement results for the platelets and the degraded platelets in the platelet preparation and the red blood cells and the white blood cells remaining in the platelet preparation are displayed in the platelet preparation+remaining blood cell measurement mode. The operator can thereby check the quality of the platelet preparation. Moreover, since the quality information is displayed on the display part 43 as described above, the operator can easily and accurately perform the quality test of the blood preparation.

Note that the standards for the blood components depending on the type of blood preparation described in FIG. 15B may be displayed in the region 703 together with the resultant values of the measurement items. Displaying the standards and the measurement results as described above allows the operator to determine the quality of the blood preparation by referring to the displayed standards and measurement results.

When the tab 730 is operated, histograms and scattergrams relating to the analysis processing in step S110 in FIG. 10 are displayed in the region 703. The controller 41 may generate the histogram and the scattergram when performing the analysis processing or generate them at the timing of the operation of the tab 730.

Figure 19A:
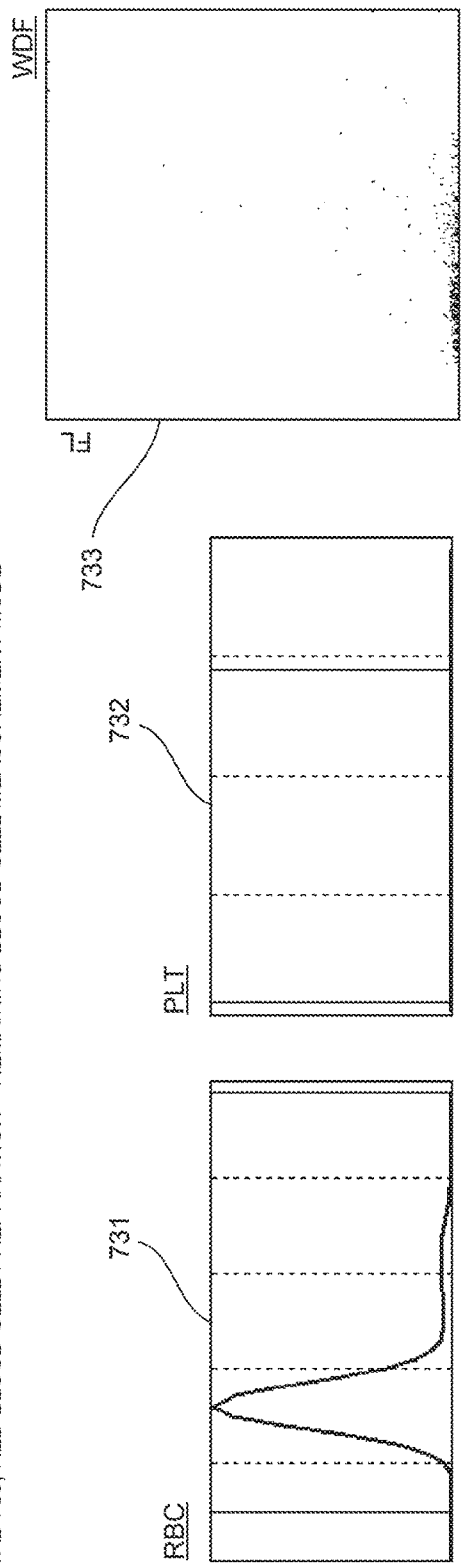
FIGS. 19A and 19B are views illustrating graphs displayed for measurement results according to an embodiment 1.

As illustrated in FIG. 19A, when the tab 730 is operated for the measurement results in the red blood cell preparation+remaining blood cell measurement mode, a RBC histogram 731 and a PLT histogram 732 generated in the RBC/PLT measurement and a WDF scattergram 733 generated in the white blood cell differential measurement are displayed in the region 703. Note that, in the red blood cell preparation measurement mode, display of the WDF scattergram 733 is omitted.

Figure 19B:
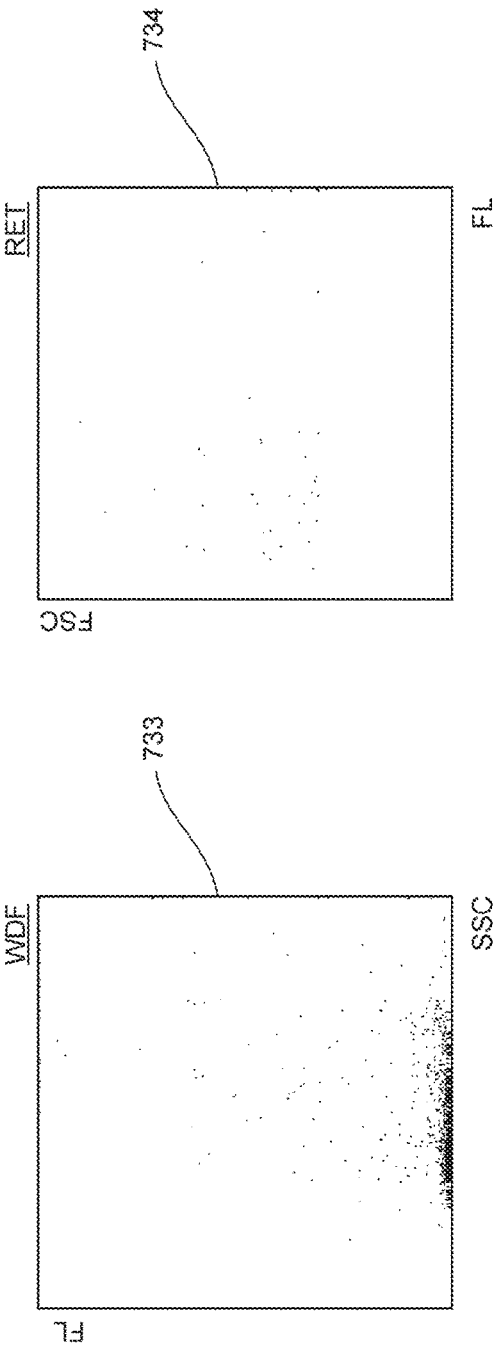

As illustrated in FIG. 19B, when the tab 730 is operated for the measurement results in the plasma preparation measurement mode, the WDF scattergram 733 generated in the white blood cell differential measurement and a RET scattergram 734 generated in the reticulocyte count measurement are displayed in the region 703.

Figure 20:
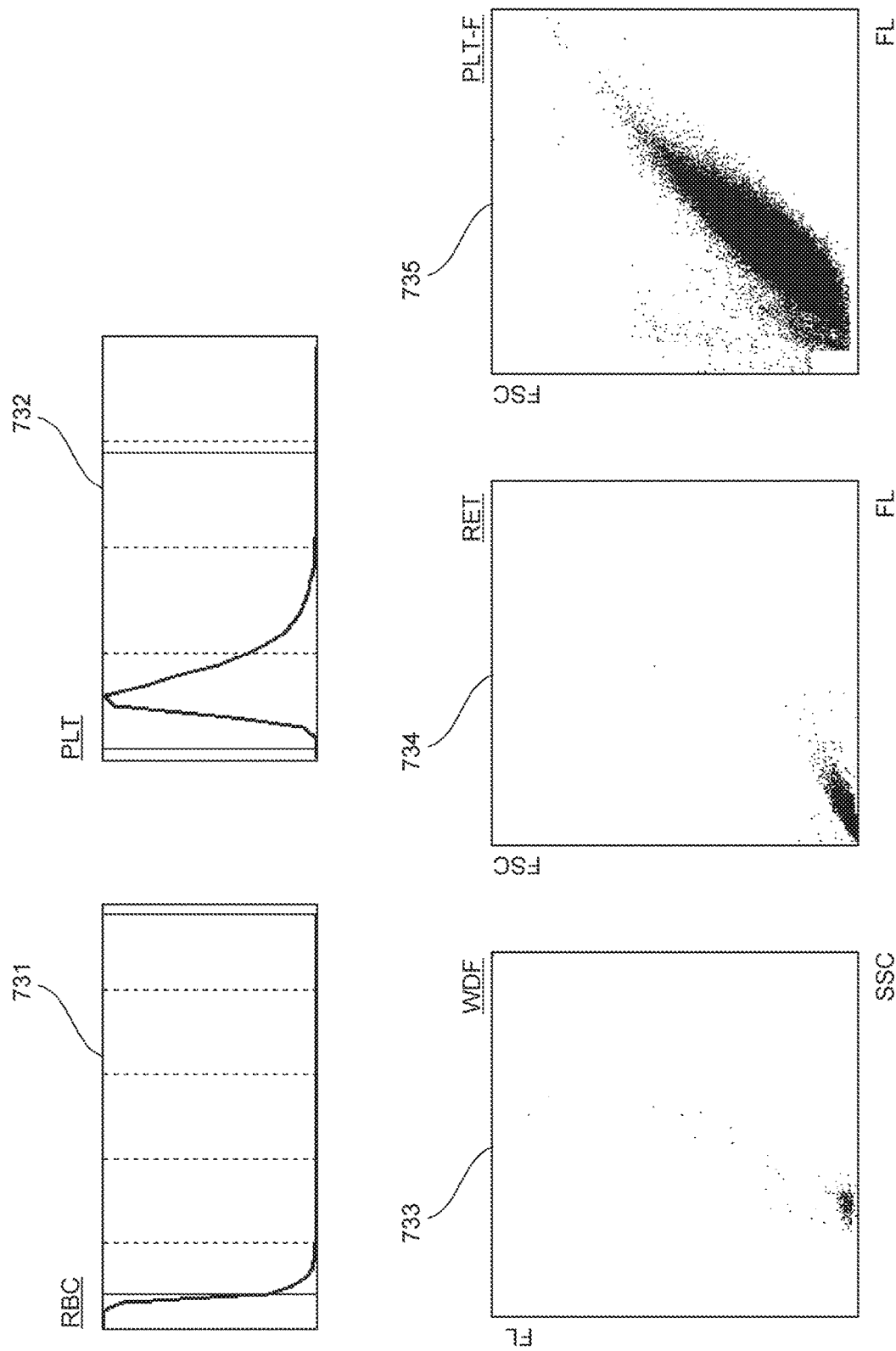
FIG. 20 is a view illustrating graphs displayed for measurement results according to an embodiment 1.

As illustrated in FIG. 20, when the tab 730 is operated for the measurement results in the platelet preparation+remaining blood cell measurement mode, the RBC histogram 731 and the PLT histogram 732 generated in the RBC/PLT measurement, the WDF scattergram 733 generated in the white blood cell differential measurement, the RET scattergram 734 generated in the reticulocyte count measurement, and a PLT-F scattergram 735 generated in the platelet count measurement (optical method) are displayed in the region 703. Note that, in the platelet preparation measurement mode, display of the WDF scattergram 733 and the RET scattergram 734 are omitted.

As illustrated in FIGS. 19A, 19B, and 20, displaying the histograms and the scattergrams generated in the respective measurements as the quality information allows the operator to grasp the quality of the blood preparation in further detail.

Note that, instead of displaying the quality information on the display part 43, the quality information in the lists and graphs may be sent to a device other than the blood analyzer 10. Moreover, the quality information in the lists may be outputted from a speaker provided in the blood analyzer 10 by means of audio. Outputting the quality information as described above allows the operator to perform the quality test of the blood preparation by checking the outputted quality information.

Next, setting of the measurement target at start-up is described with reference to the flowchart in FIG. 21A.

Figure 21B:
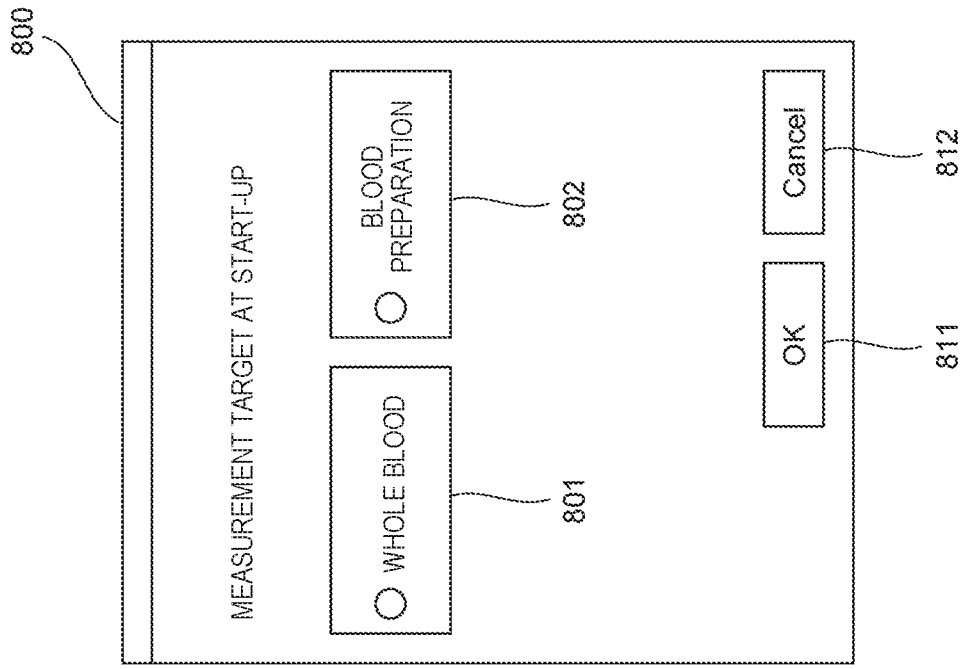
FIG. 21B is a diagram illustrating a screen for changing a measurement target in start-up according to an embodiment 1.
Figure 21A:
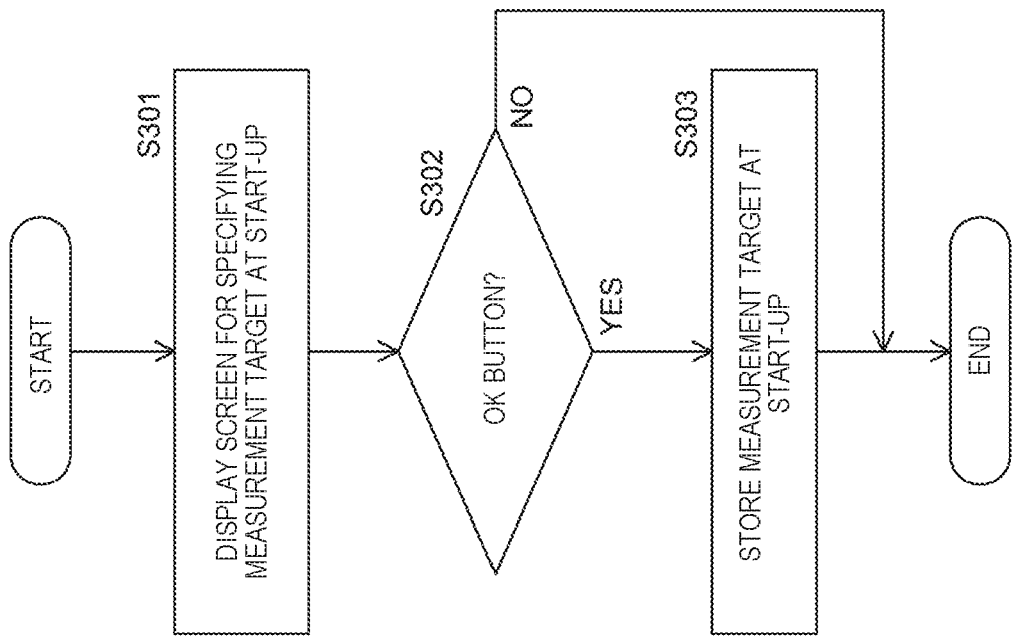
FIG. 21A is a flowchart illustrating setting of a measurement target in start-up according to an embodiment 1.

The processing in FIG. 21A is started when the operator operates a menu or the like displayed on the display part 43 to input an instruction of starting the setting of the measurement target at the start-up.

In step S301, the controller 41 displays a screen 800 for setting the measurement target at the start-up, on the display part 43. As illustrated in FIG. 21B, the screen 800 includes a button 801 for specifying the whole blood as the measurement target, a button 802 for specifying the blood preparation as the measurement target, an OK button 811, and a cancel button 812. The operator can select one of the buttons 801, 802. In step S302, the controller 41 determines whether the OK button 811 is operated.

When the operator operates the OK button 811 with one of the buttons 801, 802 being selected, in step S303, the controller 41 stores the measurement target specified by using the button 801 or the button 802 in the memory 42 as the measurement target at the start-up. Then, the controller 41 closes the screen 800. Meanwhile, when the operator operates the cancel button 812, the controller 41 cancels the measurement target selected in the screen 800 without executing step S303 and closes the screen 800.

The controller 41 sets the measurement target set as described above as the measurement target of the blood analyzer 10 when the blood analyzer 10 is started up.

Accordingly, when the blood analyzer 10 is to be used mainly for the measurement of the whole blood, the operator can set the measurement target at the start-up to the whole blood in advance through the screen 800 and thereby omit work of setting the measurement target to the whole blood through the screen 500 in FIG. 9A after the start-up of the blood analyzer 10. Similarly, when the blood analyzer 10 is to be used mainly for the measurement of the blood preparation, the operator can set the measurement target at the start-up to the blood preparation in advance through the screen 800 and thereby omit work of setting the measurement target to the blood preparation through the screen 500 in FIG. 9A after the start-up of the blood analyzer Embodiment 2

As illustrated in FIG. 22A, compared to FIG. 15A, step S211 is added after the step S20 in an embodiment 2. Moreover, in step S202 in FIG. 22A, a determination result of a blood preparation error is further displayed in response to an instruction from the operator. Configurations and other processes in an embodiment 2 are substantially the same as those in an embodiment 1.

As illustrated in FIG. 22A, in step S211, the controller 41 determines whether there is the blood preparation error based on the resultant values, that is the measurement results of the measurement items obtained in step S110 in FIG. 10 and the determination standards illustrated in FIG. 22B.

The determination standards in FIG. 22B indicate the standards for the blood components met by a different type of blood preparation from the target blood preparation. First to third rows in FIG. 22B each describe a determination standard for determining whether there is a possibility of a blood preparation, assumed to be one of the three blood preparations, being any of the other two blood preparations. As described in the first row, when: the value of the measurement item "RBC" is less than 100 cells ($10^4/\mu L$); the value of the measurement item "HGB" is less than 5 (g/dL); or the value of the measurement item "HCT" is less than 20(%) in the measurement of the red blood cell preparation, the controller 41 determines that the measured blood preparation is not the red blood cell preparation but the plasma preparation or the platelet preparation. As described in the second row, when the value of the measurement item "RBC" is greater than 50 cells ($10^4/\mu L$) in the measurement of the plasma preparation, the controller 41 determines that the measured blood preparation is not the plasma preparation but is the red blood cell preparation. As described in the third row, when the value of the measurement item "PLT" is less than 20 cells ($10^4/\mu L$) in the measurement of the platelet preparation, the controller 41 determines that the measured blood preparation is not the platelet preparation but is the red blood cell preparation or the plasma preparation.

Note that, since no platelet count measurement (optical method) is performed in the measurement of the plasma preparation, presence or absence of the platelets is difficult to determine. However, in the case where the platelet count measurement (optical method) is performed in the measurement of the plasma preparation, the controller 41 may determine that the measured blood preparation is not the plasma preparation but is the platelet preparation when the value of the measurement item "PLT" is greater than a predetermined value. Similarly, in the case where the platelet count measurement (optical method) is performed in the measurement of the red blood cell preparation, the controller 41 may determine that the measured blood preparation is not the red blood cell preparation but is the platelet preparation when the value of the measurement item "PLT" is greater than a predetermined value. Moreover, when the value of the measurement item "RBC" is greater than a predetermined value in the measurement of the platelet preparation, the controller 41 may determine that the measured blood preparation is not the platelet preparation but is the red blood cell preparation.

In step S202, the controller 41 displays the determination result of the blood preparation error in step S211 on the display part 43 together with information similar to that in an embodiment 1. For example, when the controller 41 determines that the blood preparation measured in step S211 is the plasma preparation or the platelet preparation in the case of receiving an instruction of measuring the red blood cell preparation, the controller 41 displays a region 704 illustrated in FIG. 23A in the screen 700. In the region 704 illustrated in FIG. 23A as an example, "plasma preparation? platelet preparation?" is displayed as information indicating that the blood preparation being the measurement target is the different type of blood preparation.

Moreover, when the controller 41 determines that the blood preparation measured in step S211 is the red blood cell preparation in the case of receiving an instruction of measuring the plasma preparation, the controller 41 displays the region 704 illustrated in FIG. 23B in the screen 700. In the region 704 illustrated in FIG. 23B as an example, "red blood cell preparation?" is displayed as information indicating that the blood preparation being the measurement target is the different type of blood preparation. Furthermore, when the controller 41 determines that the blood preparation measured in step S211 is the red blood cell preparation or the plasma preparation in the case of receiving an instruction of measuring the platelet preparation, the controller 41 displays the region 704 illustrated in FIG. 23C in the screen 700. In the region 704 illustrated in FIG. 23C as an example, "red blood cell preparation? plasma preparation?" is displayed as information indicating that the blood preparation being the measurement target is the different type of blood preparation.

Displaying the information indicating that the blood preparation being the measurement target is the different type of blood preparation on the display part 43 as described above allows the operator to smoothly grasp, for example, that a different blood preparation measurement mode has been erroneously selected on the reception screen 600 in FIG. 9B and that the different type of blood preparation has been erroneously stored in the container 110.

The invention includes other embodiments in addition to the above-described embodiments without departing from the spirit of the invention. The embodiments are to be considered in all respects as illustrative, and not restrictive. The scope of the invention is indicated by the appended claims rather than by the foregoing description. Hence, all configurations including the meaning and range within equivalent arrangements of the claims are intended to be embraced in the invention.

The invention claimed is:

1. A blood analyzer comprising:
an agitation part that agitates a blood preparation;
a specimen preparation part that prepares a measurement specimen by mixing a reagent with the blood preparation agitated by the agitation part;
a measurement part that measures the measurement specimen;
a display part that displays a reception screen through which a type of the blood preparation as a measurement target is selected from a plurality of types of blood preparations; and
a controller, wherein
the controller causes the agitation part to agitate the blood preparation with an intensity of agitation depending on the selected type of the blood preparation before mixing the reagent with the blood preparation, and causes the specimen preparation part to prepare the measurement specimen by mixing the reagent with the agitated blood preparation; and
the intensity of agitation for a selected type of blood preparation being a red blood cell preparation is greater than the intensity of agitation for a selected type of blood preparation being a platelet preparation.

2. The blood analyzer according to claim 1, further comprising an input device, wherein the input device receives an input of one of at least:
a red blood cell preparation measurement mode in which the red blood cell preparation is measured; and
a platelet preparation measurement mode in which the platelet preparation is measured.

3. The blood analyzer according to claim 1, wherein the controller outputs an indication of a quality of the blood preparation as compared to a quality standard depending on the selected type of blood preparation based on a measurement result of the measurement specimen.

4. The blood analyzer according to claim 3, wherein the controller determines whether the blood preparation is acceptable based on a standard for blood component corresponding to the selected type of blood preparation and the measurement result of the measurement specimen prepared from the blood preparation.

5. The blood analyzer according to claim 1, wherein the controller outputs a standard for blood component corresponding to the selected type of blood preparation and a measurement result of the measurement specimen.

6. The blood analyzer according to claim 1, wherein
the plurality of types of blood preparations comprises the red blood cell preparation, and
in a condition in which the selected type of blood preparation as the measurement target comprises the red blood cell preparation, the measurement part measures a red blood cell count in the measurement specimen.

7. The blood analyzer according to claim 1, wherein
the plurality of types of blood preparations comprises the red blood cell preparation, and
in a condition in which the selected type of blood preparation as the measurement target comprises the red blood cell preparation, the measurement part measures a white blood cell count in the measurement specimen.

8. The blood analyzer according to claim 7, wherein the controller determines whether the red blood cell preparation is acceptable based on a standard for white blood cell count and the measured white blood cell count.

9. The blood analyzer according to claim 1, wherein the plurality of types of blood preparations comprises the platelet preparation, and
in a condition in which the selected type of blood preparation as the measurement target comprises the platelet preparation, the measurement part measures a platelet count in the measurement specimen.

10. The blood analyzer according to claim 1, wherein the plurality of types of blood preparations comprises a platelet preparation, and in a condition in which the selected type of blood preparation as the measurement target comprises the platelet preparation, the measurement part measures a white blood cell count in the measurement specimen.

11. The blood analyzer according to claim 10, wherein the controller determines whether the platelet preparation is acceptable based on a standard for white blood cell count and the measured white blood cell count.

12. The blood analyzer according to claim 1, wherein
the plurality of types of blood preparations comprises the platelet preparation, and
in a condition in which the selected type of blood preparation as the measurement target comprises the platelet preparation, the measurement part measures a red blood cell count in the measurement specimen.

13. The blood analyzer according to claim 12, wherein the controller determines whether the platelet preparation is acceptable based on a standard for red blood cell count and the measured red blood cell count.

14. The blood analyzer according to claim 9, wherein
the measurement part measures a fluorescence intensity of particles in the measurement specimen, and
the controller determines whether the platelet preparation is acceptable based on the number of particles with a lower fluorescence intensity than a fluorescence intensity of platelets.

15. The blood analyzer according to claim 14, wherein the controller determines whether the platelet preparation is acceptable based on a standard for the number of particles with the lower fluorescence intensity in the platelet preparation and the measured number of particles with the lower fluorescence intensity.

16. The blood analyzer according to claim 1, wherein
the plurality of types of blood preparations comprises a plasma preparation, and
in a condition in which the selected type of blood preparation as the measurement target comprises the plasma preparation, the measurement part measures a white blood cell count in the plasma preparation.

17. The blood analyzer according to claim 16, wherein the controller determines whether the plasma preparation is acceptable based on a standard for white blood cell count and the measured white blood cell count.

18. The blood analyzer of claim 1, wherein the intensity of agitation for a selected type of blood preparation being a red blood cell preparation is greater than the intensity of agitation for a selected type of blood preparation being a plasma preparation.

* * * * *